(12) United States Patent
Chiu et al.

(10) Patent No.: US 7,419,501 B2
(45) Date of Patent: Sep. 2, 2008

(54) INTEGRATED MECHANICAL HANDLE WITH QUICK SLIDE MECHANISM

(75) Inventors: Brian Chiu, Sunnyvale, CA (US); Ari Gershman, Moraga, CA (US); Burt Goodson, Fremont, CA (US); Paul L. Weber, Hudson, WI (US); Richard E. Repp, San Jose, CA (US); David F. Jensen, Sunnyvale, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 19 days.

(21) Appl. No.: 11/460,551

(22) Filed: Jul. 27, 2006

(65) Prior Publication Data

US 2006/0265045 A1 Nov. 23, 2006

Related U.S. Application Data

(60) Division of application No. 10/752,237, filed on Jan. 5, 2004, now Pat. No. 7,105,016, which is a continuation-in-part of application No. 10/128,956, filed on Apr. 23, 2002, now Pat. No. 6,911,039.

(51) Int. Cl.
*A61F 2/06* (2006.01)
(52) U.S. Cl. .................................. 623/1.12; 623/1.23
(58) Field of Classification Search ................ 623/1.11, 623/1.12, 1.23; 606/108
See application file for complete search history.

(56) References Cited

U.S. PATENT DOCUMENTS

| | | | |
|---|---|---|---|
| 1,827,497 A | 10/1931 | Varney | |
| 4,723,938 A | 2/1988 | Goodin et al. | |
| 4,832,692 A | 5/1989 | Box et al. | |
| 5,137,514 A | 8/1992 | Ryan | |
| 5,197,971 A | 3/1993 | Bonutti | |
| 5,215,523 A | 6/1993 | Williams et al. | |
| 5,259,838 A | 11/1993 | Taylor et al. | |
| 5,263,969 A | 11/1993 | Phillips | |
| 5,344,426 A | 9/1994 | Lau et al. | |
| 5,345,927 A | 9/1994 | Bonutti | |
| 5,358,496 A | 10/1994 | Oritz et al. | |
| 5,433,723 A | 7/1995 | Lindenberg et al. | |
| 5,449,344 A | 9/1995 | Taylor et al. | |
| 5,462,659 A | 10/1995 | Saxena et al. | |
| 5,507,727 A | 4/1996 | Crainich | |
| 5,507,768 A | 4/1996 | Lau et al. | |
| 5,534,007 A | 7/1996 | St. Germain et al. | |
| 5,571,168 A | 11/1996 | Toro | |
| 5,683,451 A | 11/1997 | Lenker et al. | |

(Continued)

FOREIGN PATENT DOCUMENTS

EP 1117341 7/2001

(Continued)

*Primary Examiner*—Thomas J Sweet

(57) ABSTRACT

A method of deploying a prosthesis includes engaging a hub assembly of a handle to a threaded outer surface of a slide shaft of the handle; rotating the hub assembly to cause axial translation of the hub assembly and a sheath coupled to the hub assembly to initiate deployment of the prosthesis; disengaging the hub assembly from the threaded outer surface by pivoting a thread tooth of the hub assembly out of threaded engagement with the threaded outer surface; and sliding the hub assembly on the slide shaft to further retract the sheath and complete deployment of the prosthesis.

19 Claims, 14 Drawing Sheets

U.S. PATENT DOCUMENTS

| | | | |
|---|---|---|---|
| 5,707,376 A | 1/1998 | Kavteladze et al. | |
| 5,733,267 A | 3/1998 | Del Toro | |
| 5,776,142 A | 7/1998 | Gunderson | |
| 5,782,855 A * | 7/1998 | Lau et al. | 623/1.11 |
| 5,788,707 A | 8/1998 | Del Toro et al. | |
| 5,797,952 A | 8/1998 | Klein | |
| 5,824,058 A | 10/1998 | Ravenscroft et al. | |
| 5,860,955 A | 1/1999 | Wright et al. | |
| 5,906,619 A | 5/1999 | Olson et al. | |
| 5,954,742 A | 9/1999 | Osypka | |
| 5,968,052 A | 10/1999 | Sullivan, III et al. | |
| 6,042,588 A | 3/2000 | Munsinger et al. | |
| 6,110,151 A * | 8/2000 | Spool et al. | 604/218 |
| 6,117,142 A | 9/2000 | Goodson et al. | |
| 6,146,415 A | 11/2000 | Fitz | |
| 6,203,550 B1 | 3/2001 | Olson | |
| 6,508,790 B1 | 1/2003 | Lawrence | |
| 2002/0004676 A1 | 1/2002 | Berryman et al. | |
| 2002/0111666 A1 | 8/2002 | Hart et al. | |
| 2003/0074043 A1 | 4/2003 | Thompson | |
| 2003/0074045 A1 | 4/2003 | Buzzard et al. | |
| 2003/0199966 A1 | 10/2003 | Shiu et al. | |
| 2004/0127912 A1 | 7/2004 | Rabkin et al. | |

FOREIGN PATENT DOCUMENTS

| | | |
|---|---|---|
| EP | 1302178 | 4/2003 |
| WO | WO 03/068302 | 8/2003 |

* cited by examiner

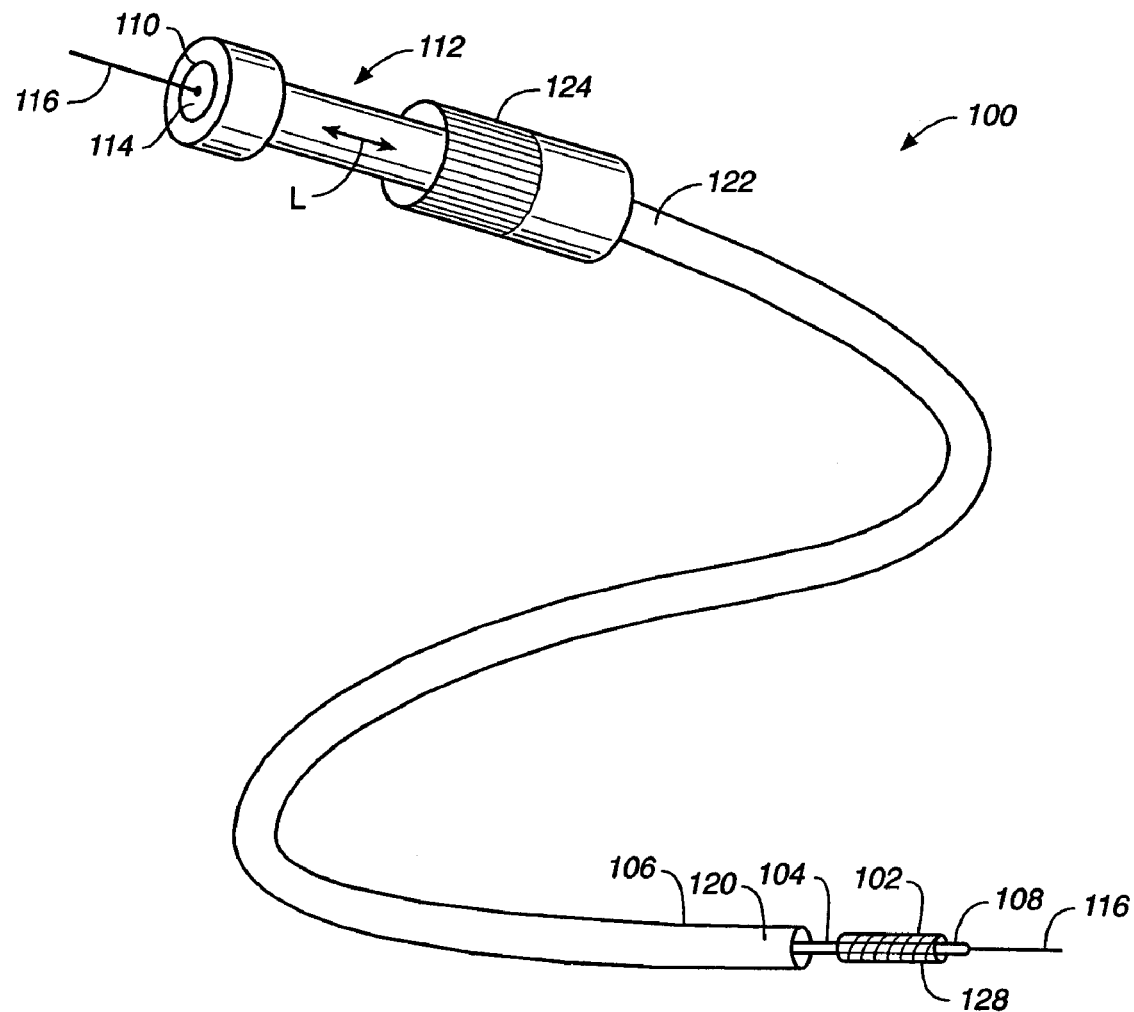
FIG._1

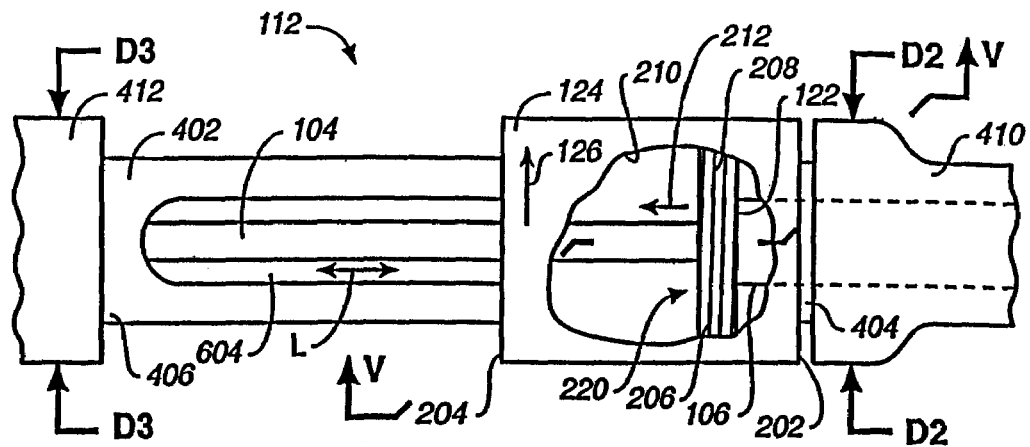
FIG._2
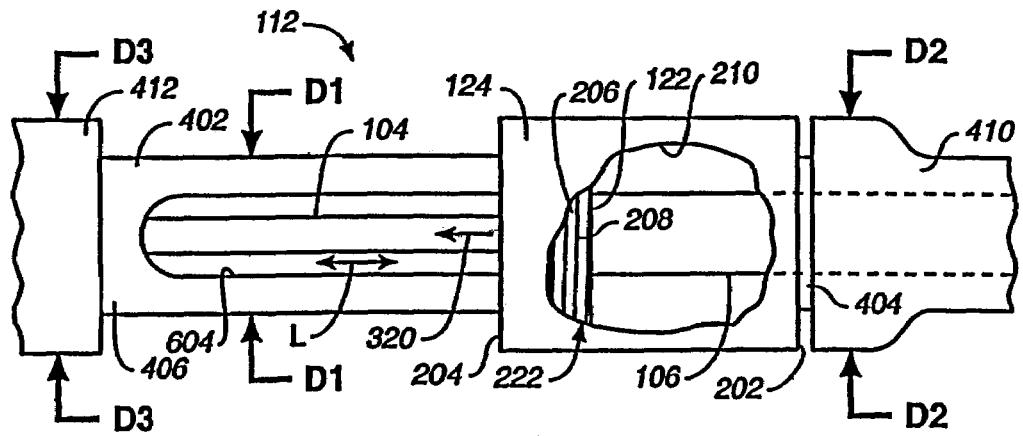
FIG._3
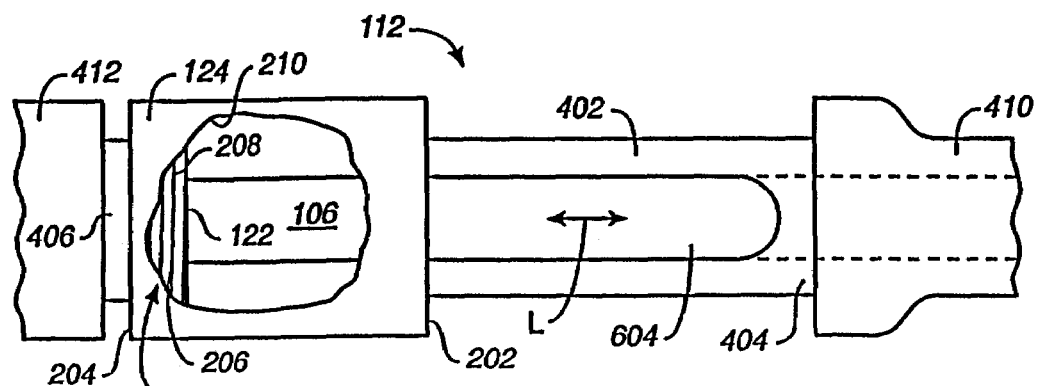
FIG._4

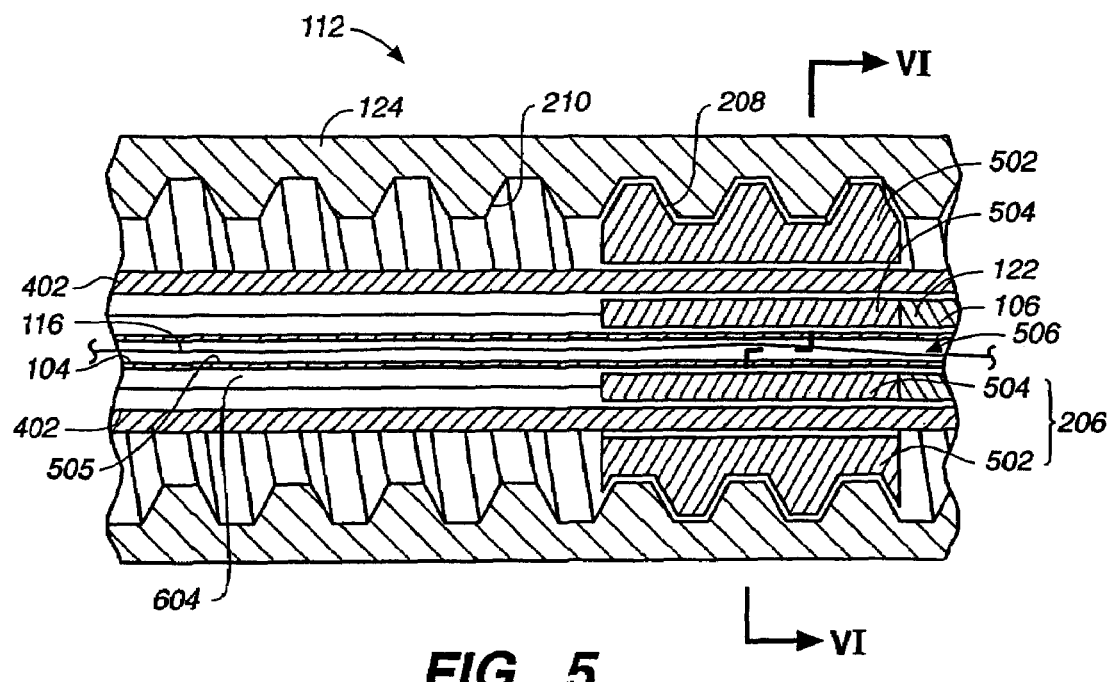
*FIG._5*
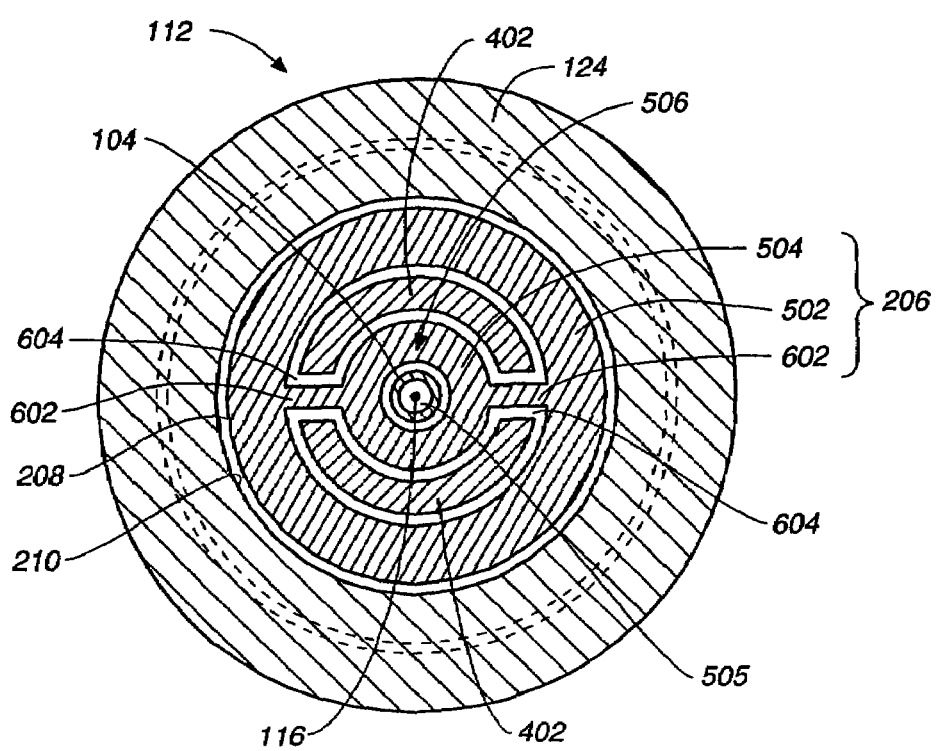
*FIG._6*

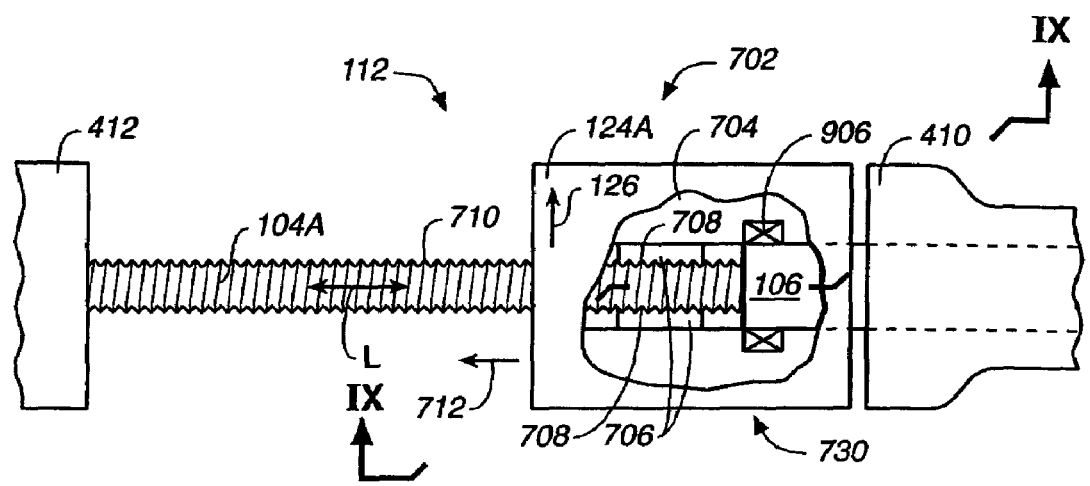
FIG._7
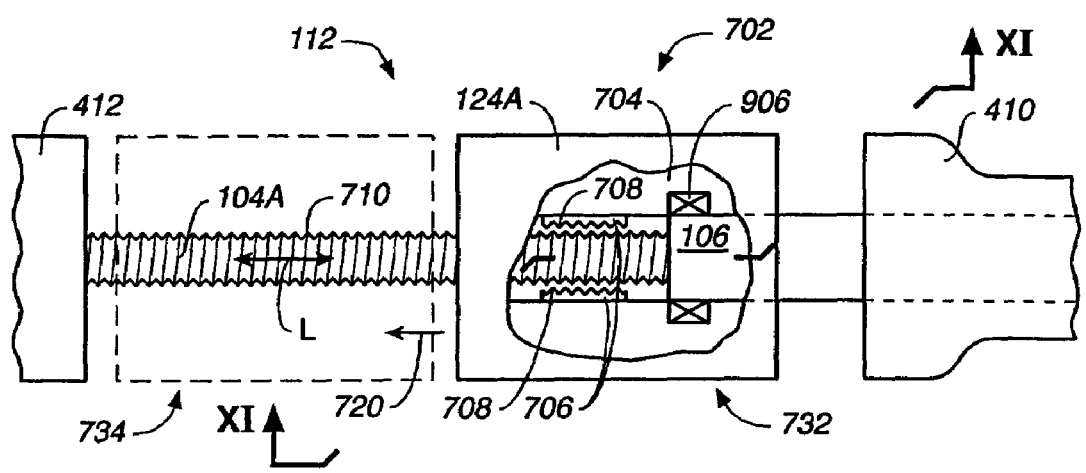
FIG._8

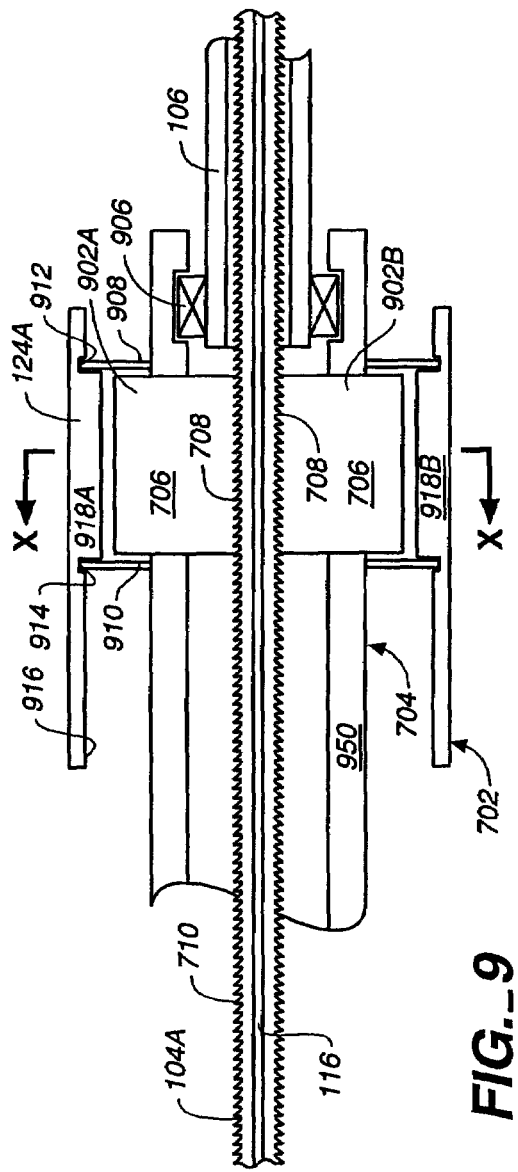
FIG._9
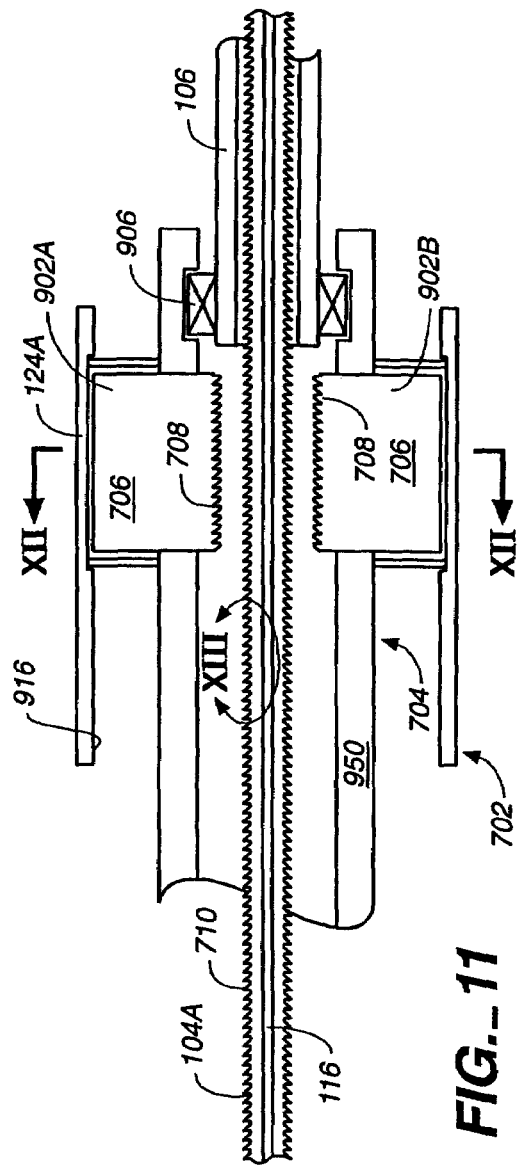
FIG._11

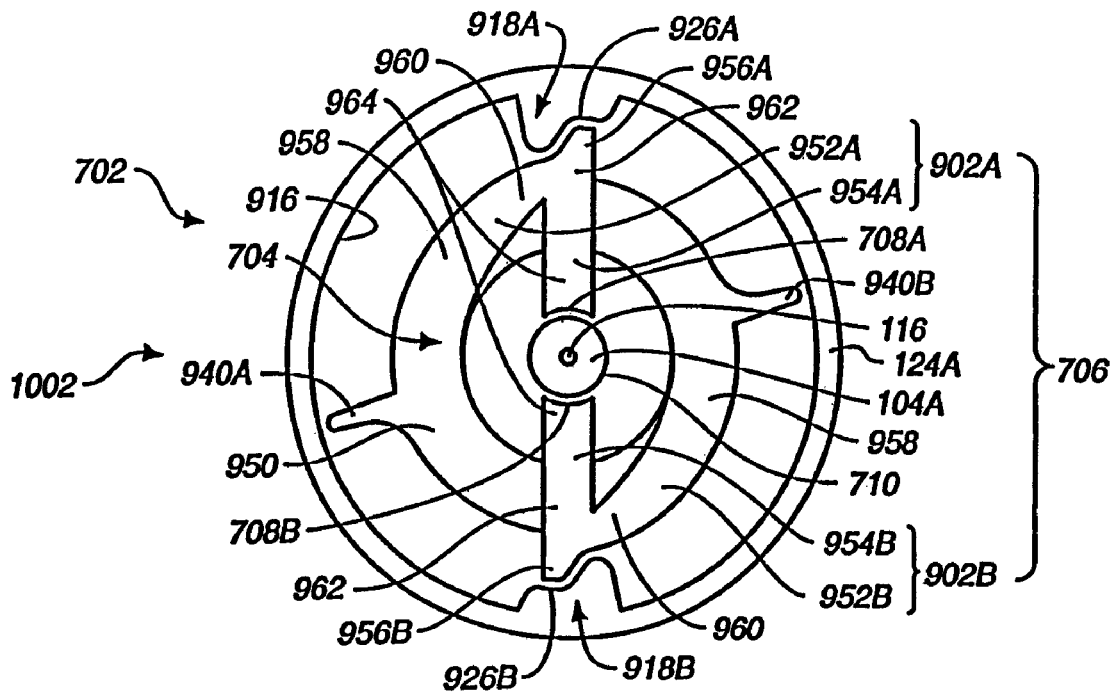
FIG._10
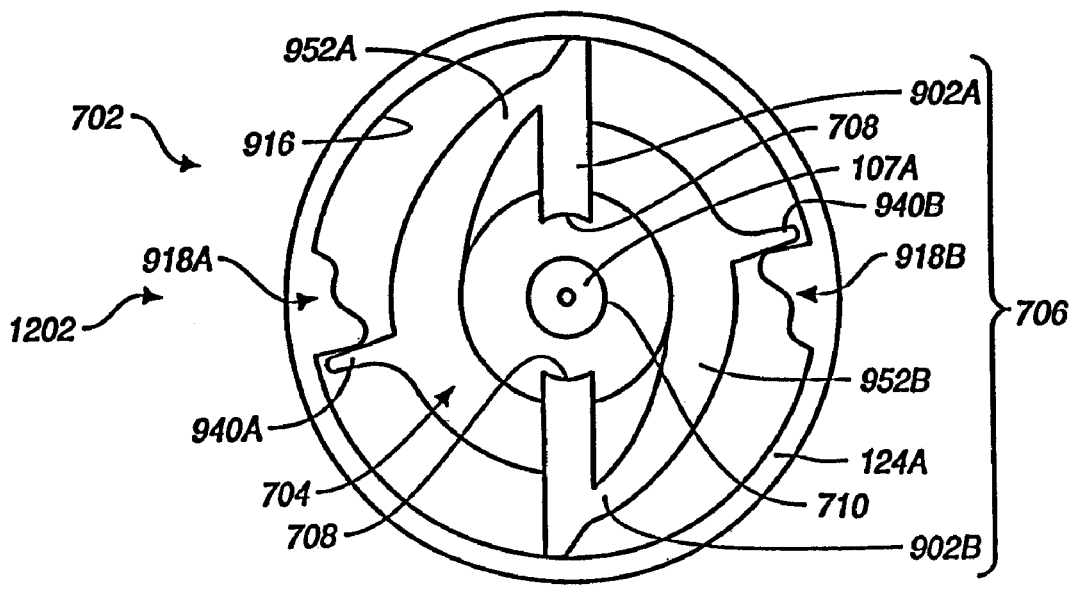
FIG._12

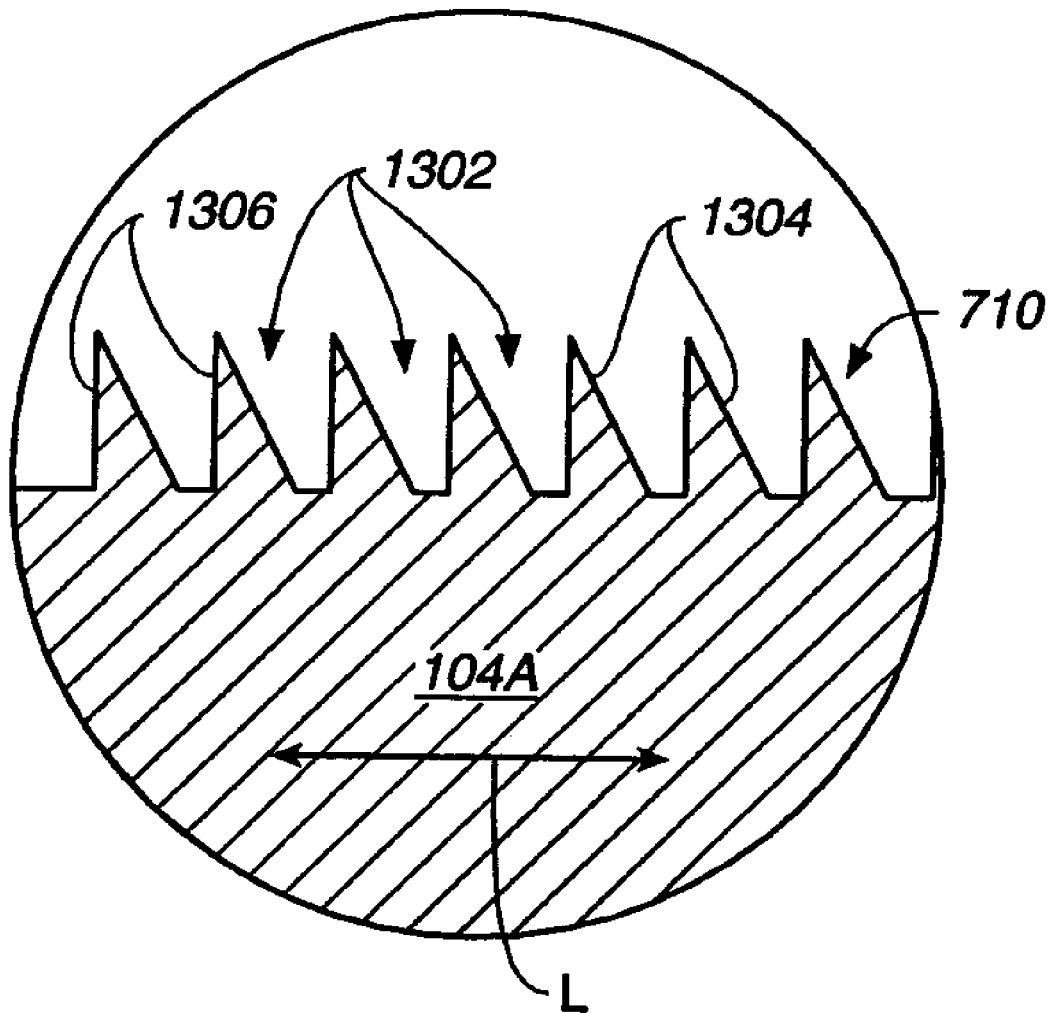
FIG._13

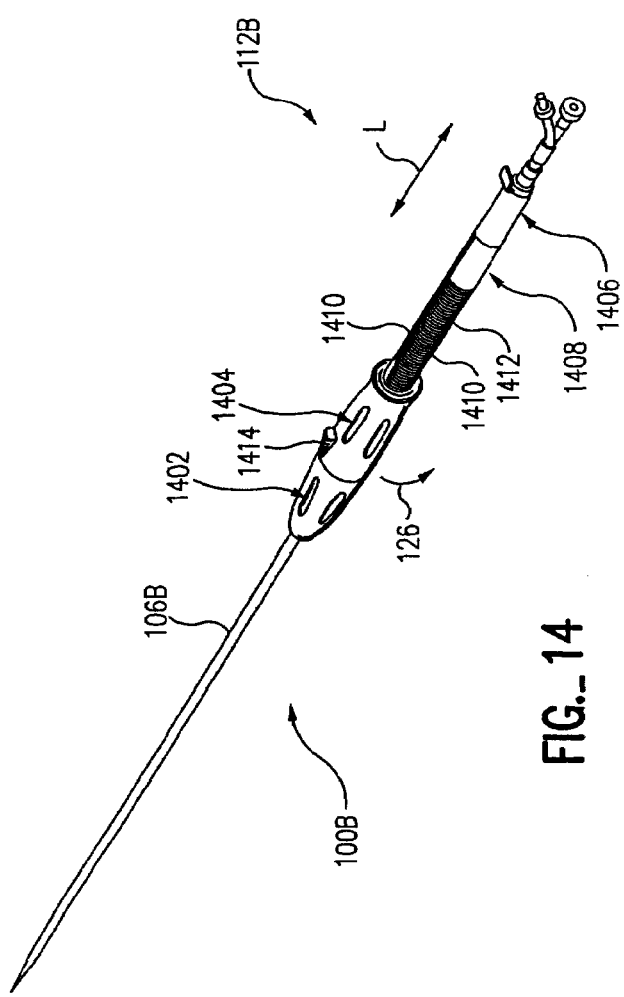
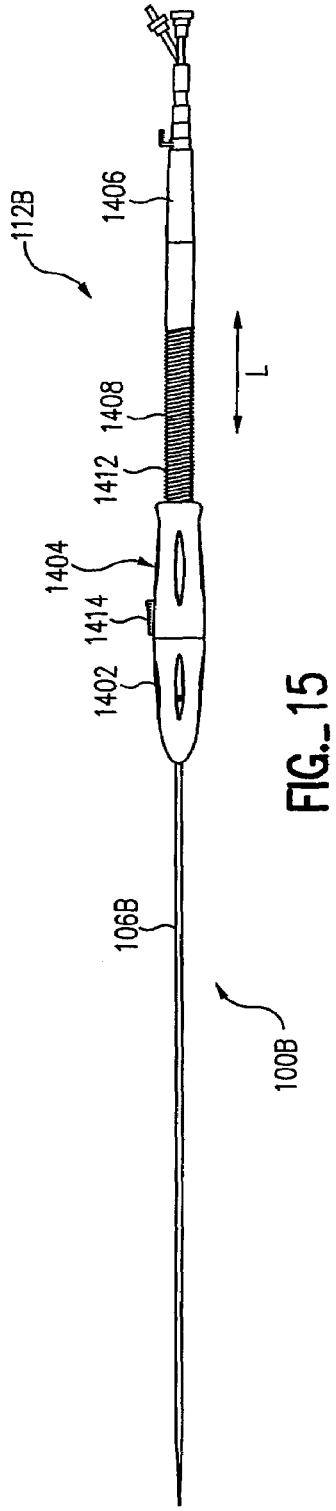

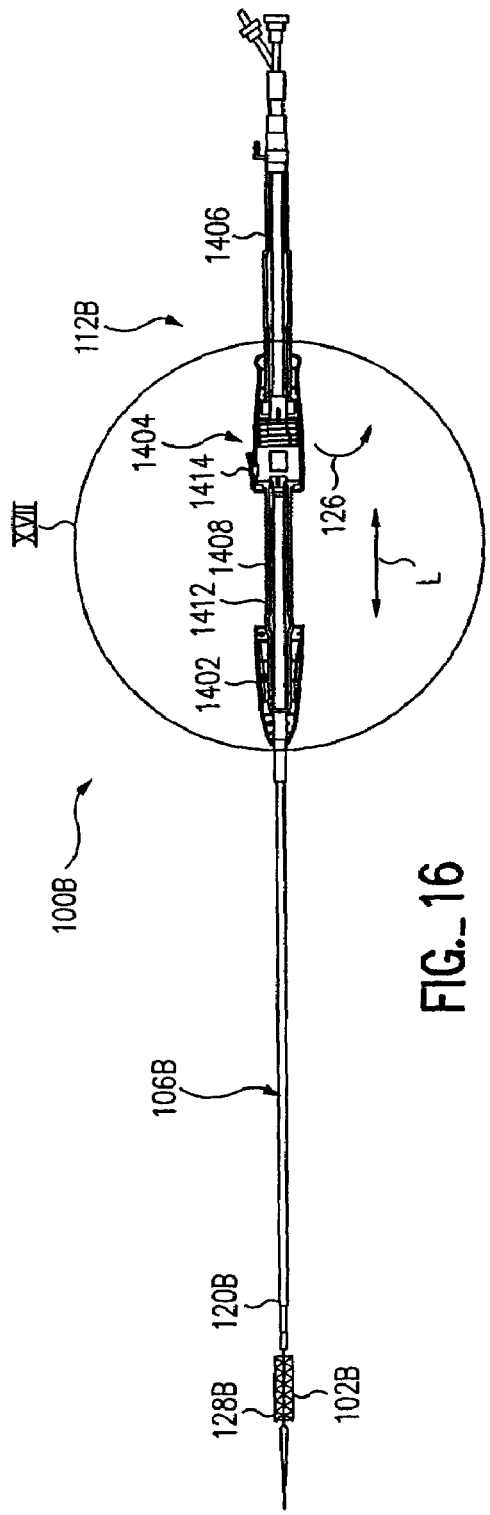
FIG._16
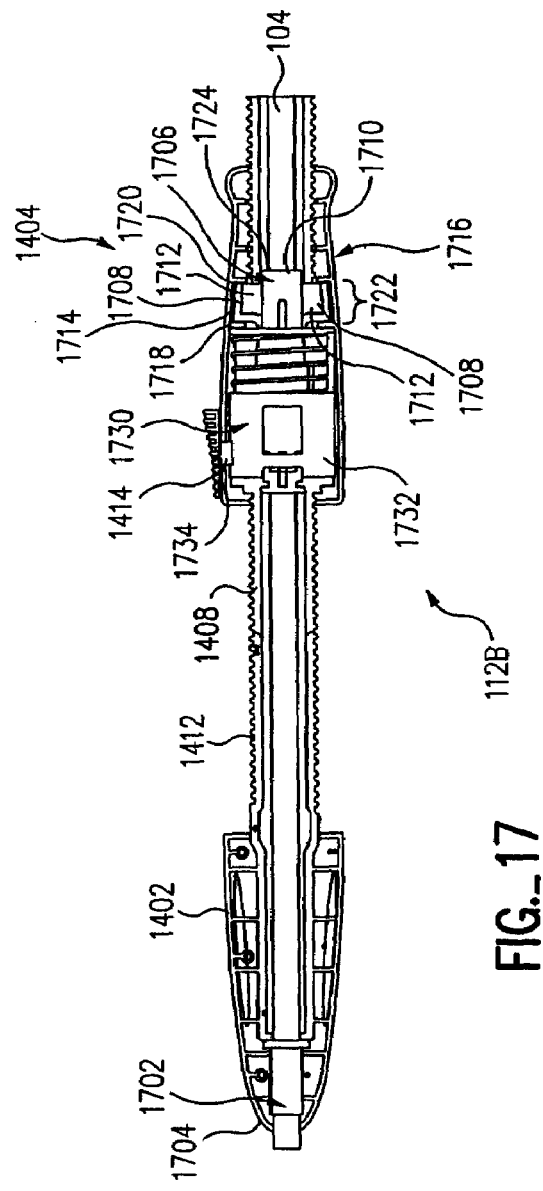
FIG._17

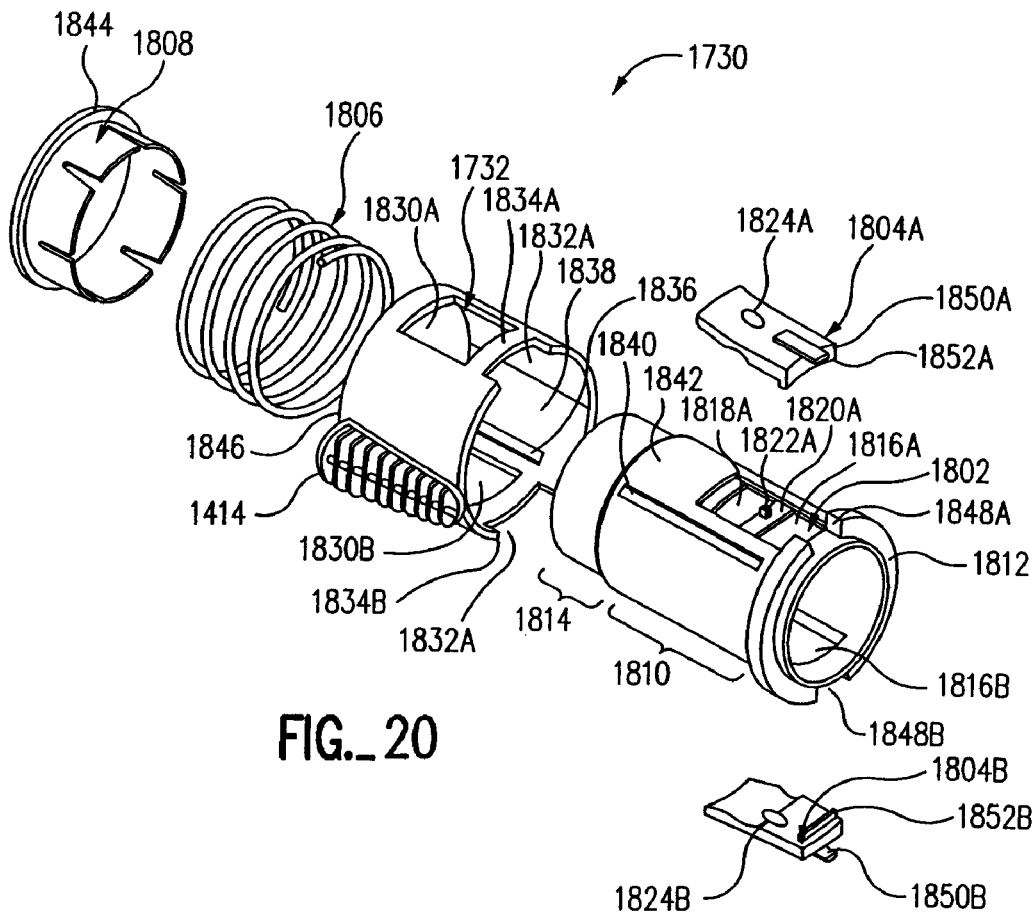
FIG._20
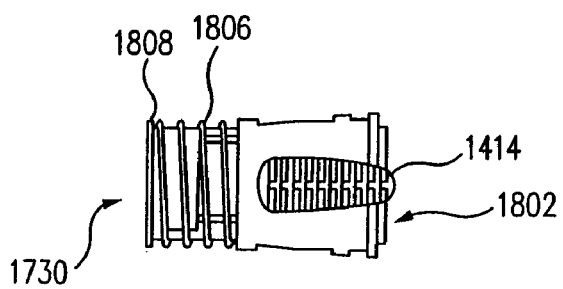
FIG._19
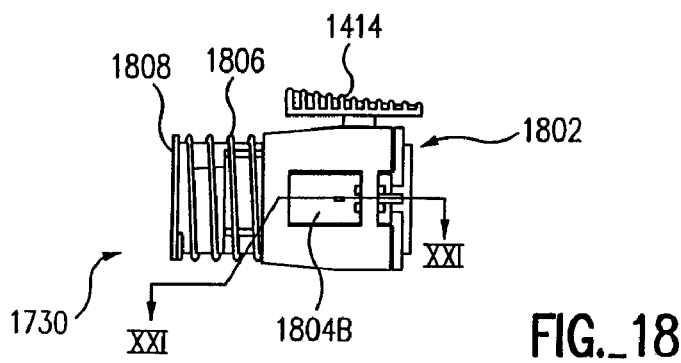
FIG._18

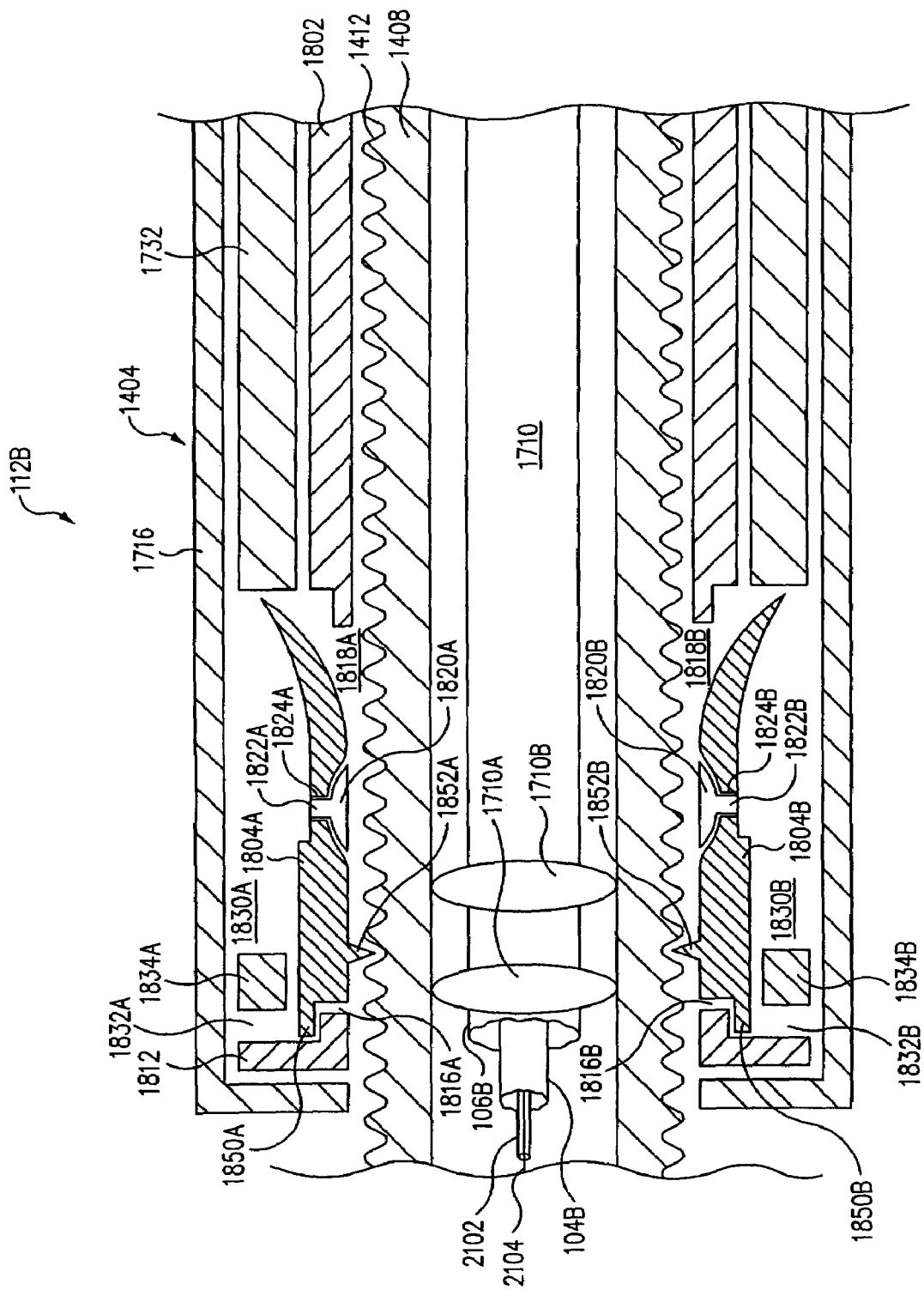
FIG._21

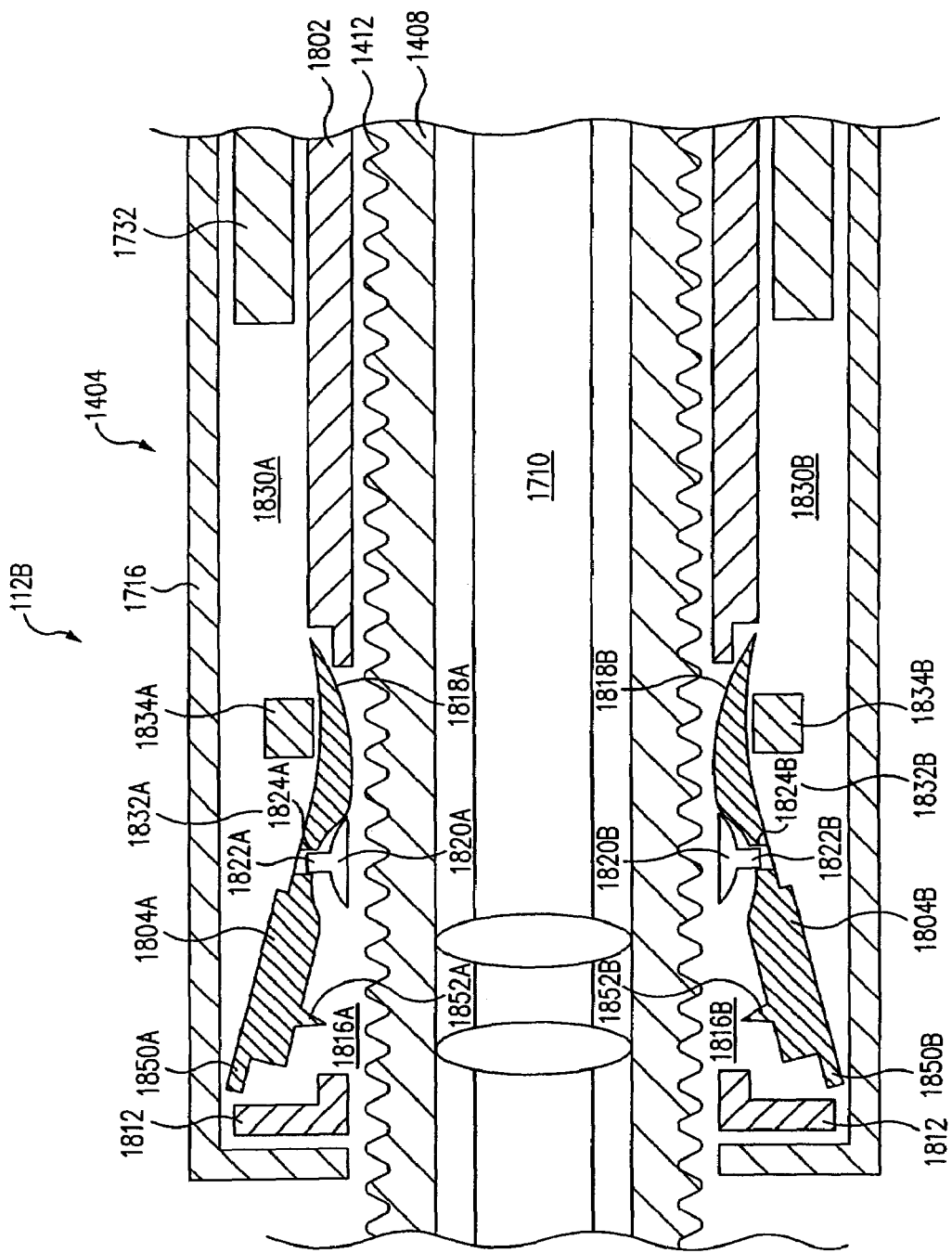
FIG._22

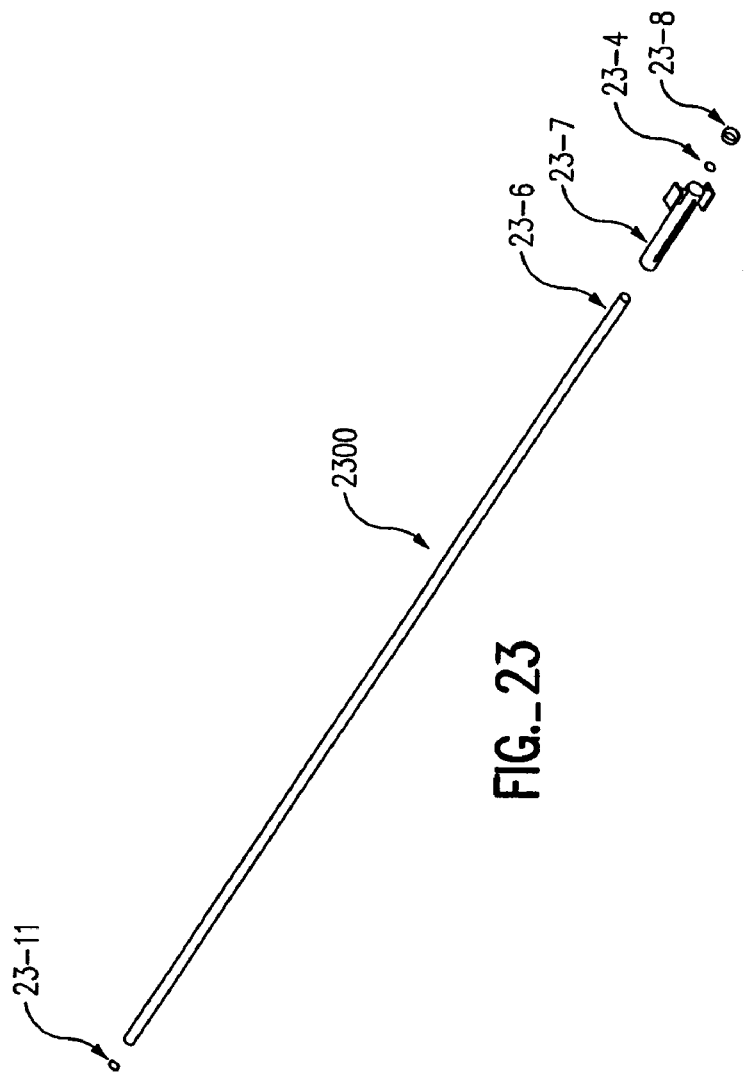
FIG._23
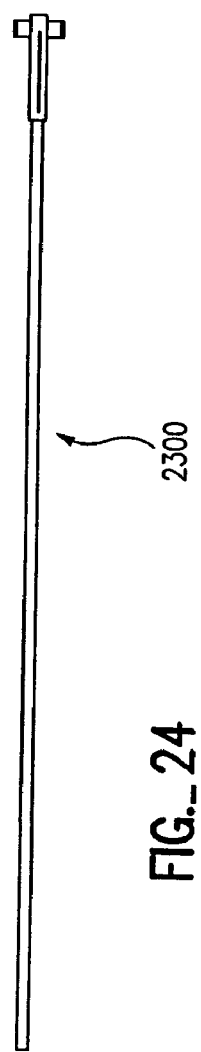
FIG._24

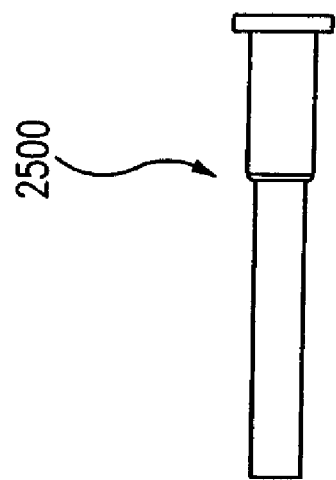
FIG._26
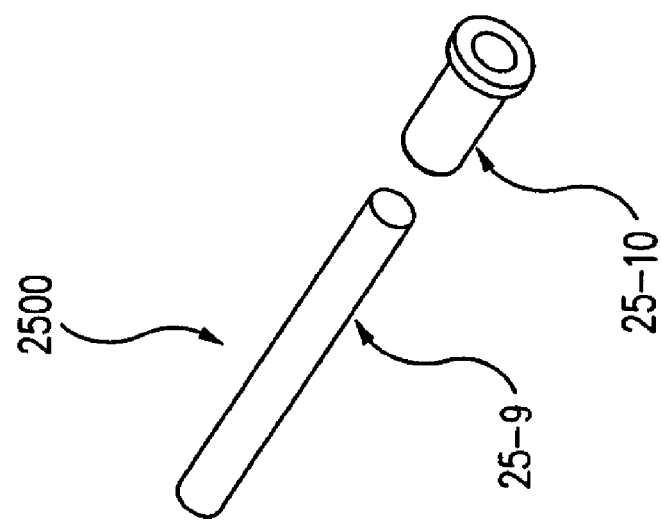
FIG._25

INTEGRATED MECHANICAL HANDLE WITH QUICK SLIDE MECHANISM

CROSS-REFERENCE TO RELATED APPLICATIONS

This application is a Divisional of U.S. patent application Ser. No. 10/752,237, filed on Jan. 5, 2004, now U.S. Pat. No. 7,105,016, issued Sep. 12, 2006, which is a Continuation-in-part of U.S. patent application Ser. No. 10/128,956, filed on Apr. 23, 2002, now U.S. Pat. No. 6,911,039, issued Jun. 28, 2005.

BACKGROUND OF THE INVENTION

1. Field of the Invention

The present invention relates to an intra-vascular device and method. More particularly, the present invention relates to a delivery system for deploying endoluminal prostheses within the lumens of the body and to a method of using the same.

2. Description of the Related Art

Vascular aneurysms were the result of abnormal dilation of a blood vessel, usually resulting from disease and/or genetic predisposition, which weakened the arterial wall and allowed it to expand. While aneurysms could occur in any blood vessel, most occurred in the aorta and peripheral arteries, with the majority of aortic aneurysms occurring in the abdominal aorta, usually beginning below the renal arteries and often extending into one or both of the iliac arteries.

Aortic aneurysms were commonly treated in open surgical procedures where the diseased vessel segment was bypassed and repaired with an artificial vascular graft. While considered to be an effective surgical technique, particularly considering the alternative of a usual fatal ruptured abdominal aortic aneurysm, conventional vascular graft surgery suffered from a number of disadvantages. The surgical procedure was complex and required experienced surgeons and well-equipped surgical facilities. Even with the best surgeons and equipment, however, patients being treated frequently were elderly and weakened from cardiovascular and other diseases, reducing the number of eligible patients.

Even for eligible patients prior to rupture, conventional aneurysm repair had a relatively high mortality rate, usually from 2% to 10%. Morbidity related to the conventional surgery includes myocardial infarction, renal failure, impotence, paralysis, and other conditions. Additionally, even with successful surgery, recovery took several weeks, and often required a lengthy hospital stay.

In order to overcome some or all of these drawbacks, endovascular prosthesis placement for the treatment of aneurysms has been used. Although very promising, many of the proposed methods and apparatus suffered from undesirable limitations. In particular, accurate delivery and placement of the endovascular prosthesis within the vasculature was problematic.

Stent-grafts (endovascular prosthesis) were resilient structures, usually biased to expand against the surrounding lumenal wall. Such resiliently-expanding stent-grafts were tightly compressed within the catheter, imposing significant radial expansion forces against the surrounding catheter sheath. This often lead to excess friction between the stent-graft and the sheath, particularly when the resiliently-expanding structure invaginated into the catheter material. Thus, the delivery system had to be capable of imparting a significant, yet controlled, force to retract the sheath and deploy the stent-grafts.

SUMMARY OF THE INVENTION

An embodiment according to the present invention includes, a method of deploying a prosthesis having the step of restraining the prosthesis within a proximal end of a sheath. A slide ring of a handle engaged with threads in the handle is rotated in a first direction to initiate a force for the retraction of the sheath. The slide ring is slid to complete retraction of the sheath and deploy the prosthesis.

As a result, a proximal end of the prosthesis, which is deployed first, is very gradually released by rotating the slide ring. In this manner, the physician is allowed to verify the accuracy of the deployment position as the prosthesis initially engages the surrounding body lumen.

However, since dynamic frictional forces are typically lower than static frictional forces, the frictional resistance, due to the forces between the prosthesis and the sheath, decreases once the sheath begins to move. Additionally, as the sheath moves (retracts), more and more of the prosthesis is exposed by the sheath. For this additional reason, the frictional resistance, due to the force between the prosthesis and the sheath, decreases once the sheath begins to move. Further, once the proximal end of the prosthesis has firmly engaged the surrounding body lumen, the relationship between the prosthesis and the surrounding body lumen is largely set, so that deployment can proceed safely and at a more rapid rate.

Thus, after retraction of the sheath is initiated by axial rotation of the slide ring, which moves axially because of the engagement of threaded pieces, the sheath is further retracted by sliding (manual pulling) of the slide ring. By sliding the slide ring, the sheath is easily and quickly retracted thus rapidly completing deployment of the prosthesis. Rapid deployment of the prosthesis facilitates faster procedure times, thus minimizing the period of time during which blood flow is occluded.

In accordance with another embodiment according to the present invention, a delivery system includes a handle and a sheath slidably and threadedly coupled to the handle.

In yet another embodiment according to the present invention, a delivery system includes a handle having: a slide shaft having at least one slot; a slide ring; a slide threadedly attached to the slide ring, the slide having: an inner body inside the slide shaft; an outer body outside the slide shaft; and a coupler coupling the inner body to the outer body through the at least one slot, wherein the slide ring and the slide are slidably mounted to the slide shaft.

In another embodiment, a delivery system includes: a sheath having a pushrod lumen; a pushrod extending through the sheath; and a handle having a hub assembly coupled to the sheath, the hub assembly having a selectively engaging member for selectively engaging and disengaging the hub assembly from the pushrod.

In another embodiment, a delivery system includes: a sheath and a handle. The handle includes: a slide shaft having a threaded outer surface; and a hub assembly coupled to the sheath. The hub assembly includes an internal slider subassembly for selectively engaging and disengaging the hub assembly with the threaded outer surface.

In another embodiment, a delivery system includes a sheath and a handle. The handle includes: a slide shaft having a threaded outer surface; and a hub assembly coupled to the sheath. The hub assembly includes: an inner slider having a thread tooth pivot support; a thread tooth pivotably mounted to the thread tooth pivot support; and a sleeve having a thread tooth press member pressing on the thread tooth, where motion of the sleeve relative to the inner slider pivots the thread tooth on the thread tooth pivot support to engage and disengage the hub assembly with the threaded outer surface.

In yet another embodiment, a method includes: engaging a hub assembly of a handle to a threaded outer surface of a slide shaft of the handle; rotating the hub assembly to cause axial translation of the hub assembly and a sheath coupled to the hub assembly; disengaging the hub assembly from the threaded outer surface by pivoting a thread tooth of the hub assembly out of threaded engagement with the threaded outer surface; and sliding the hub assembly on the slide shaft to further retract the sheath.

Embodiments according to the present invention are best understood by reference to the following detailed description when read in conjunction with the accompanying drawings.

BRIEF DESCRIPTION OF THE DRAWINGS

FIG. 1 is a perspective view of a delivery system for deploying a prosthesis in one embodiment according to the present invention;

FIG. 2 is a close up partial cutaway view of a handle of FIG. 1 before retraction of a sheath;

FIGS. 3 and 4 are close up partial cutaway views of the handle of FIG. 2 during retraction of the sheath;

FIG. 5 is a partial cross-sectional view of the handle taken at V-V of FIG. 2;

FIG. 6 is a cross-sectional view of the handle taken at VI-VI of FIG. 5;

FIG. 7 is a close up partial cutaway view of the handle of FIG. 1 before retraction of the sheath in another embodiment according to the present invention;

FIG. 8 is a close up partial cutaway view of the handle of FIG. 7 during retraction of the sheath;

FIG. 9 is a cross-sectional view of the handle of FIG. 7 taken at IX-IX;

FIG. 10 is a cross-sectional view of the handle taken at X-X of FIG. 9;

FIG. 11 is a cross-sectional view of the handle taken at XI-XI of FIG. 8;

FIG. 12 is a cross-sectional view of the handle taken at XII-XII of FIG. 11;

FIG. 13 is an enlarged cross-sectional view of region XIII of a pushrod of FIG. 11;

FIGS. 14 and 15 are perspective and side views of another embodiment according to the present invention;

FIG. 16 is a side view, partially in cross-section, of the delivery system of FIGS. 14 and 15 after retraction of a sheath;

FIG. 17 is an enlarged side view, partially in cross-section, of the region XVII of the handle of FIG. 16;

FIGS. 18, 19 and 20 are side, top and exploded views of an internal slider subassembly;

FIG. 21 is a cross-sectional and partially cutaway view of the handle along the line XXI-XXI of FIG. 18 with a hub assembly engaged with a threaded outer surface of a slide shaft;

FIG. 22 is a cross-sectional view of the handle of FIG. 21 with the gear teeth engagement of the hub assembly disengaged from the threaded outer surface of the slide shaft;

FIGS. 23 and 24 are exploded and side views, respectively, of a graft cover subassembly and RO marker of the delivery system of FIG. 14; and FIGS. 25 and 26 are exploded and side views, respectively, of a strain relief subassembly of the delivery system of FIG. 14.

Common reference numerals are used throughout the drawings and detailed description to indicate like elements.

DETAILED DESCRIPTION

In one embodiment, a method of deploying a prosthesis 102 (FIG. 1) includes restraining prosthesis 102 within a distal end 120 of a sheath 106. A slide ring 124 of a handle 112 is rotated in a first direction as indicated by an arrow 126 (FIG. 2) to initiate retraction of sheath 106. Slide ring 124 is slid (FIGS. 3, 4) to complete retraction of sheath 106 and deploy prosthesis 102 (FIG. 1).

In this manner, prosthesis 102 is initially very gradually released by rotating slide ring 124. This allows the physician to verify the accuracy of the deployment position as prosthesis 102 initially engages the surrounding body lumen.

However, after retraction of sheath 106 is initiated by rotation of slide ring 124 with respect to handle 112, retraction of sheath 106 is completed by sliding of slide ring 124 along the longitudinal axis of handle 112. In this manner, sheath 106 is easily and quickly retracted thus rapidly completing deployment of prosthesis 102. Rapid deployment of prosthesis 102 facilitates faster procedure times, thus minimizing the period of time during which blood flow is occluded.

More particularly, FIG. 1 is a perspective view of a delivery system 100 for deploying a prosthesis 102 in one embodiment according to the present invention. For example, prosthesis 102 is a radially expandable tubular prosthesis such as a stent or stent-graft and is used to treat one of several vascular conditions: abdominal aortic aneurysms, thoracic aortic aneurysm, or thoracic aortic dissections.

Delivery system 100 includes a pushrod 104 and a sheath 106, sometimes called a catheter sheath. Pushrod 104 includes a distal end 108 and a proximal end 110. Prosthesis 102 is placed over a portion of the distal end 108 of pushrod 104. In one embodiment, distal end 108 further includes radiopaque markers that allow the location of distal end 108 and proximal end of the prosthesis 102 (the proximal end of the delivery system is referenced with respect to the operator's handle while the proximal end of the prosthesis is referenced with respect to the end closest to the heart (via the length of blood traveled from the heart) to be precisely tracked. Proximal end 110 of pushrod 104 terminates within and is mounted to a handle 112 or extends through handle 112 and out a port 114 of handle 112.

In this embodiment, pushrod 104 is a hollow tube whose interior acts as a guide wire lumen. A guide wire 116 extends through pushrod 104 and extends out distal end 108. Guide wire 116 further extends through handle 112 and out port 114.

Sheath 106 includes a distal end 120 and a proximal end 122. Prior to deployment, prosthesis 102 is radially compressed and restrained within distal end 120 of sheath 106. Proximal end 122 of sheath 106 extends into handle 112. As discussed further below, proximal end 122 of sheath 106 is slidably and threadedly coupled to handle 112. Sheath 106 is a hollow tube which acts as a pushrod lumen. Pushrod 104 extends through sheath 106.

During use, prosthesis 102 is placed over a portion of the distal end 108 of pushrod 104 and is radially compressed and restrained within distal end 120 of sheath 106. Prosthesis 102 is introduced intra-vascularly and guided to the treatment site, e.g., an aneurysm. Once prosthesis 102 is properly positioned, sheath 106 is retracted by manipulating handle 112 thus deploying prosthesis 102.

In one embodiment, prosthesis 102 is self-expandable. In accordance with this embodiment, as sheath 106 is retracted, the released portion of the prosthesis 102 self-expands and is permanently deployed, e.g., anchored within a lumen of a patient.

The guiding of prosthesis and deployment of a self-expanding prosthesis are well known to those of skill in the art.

FIG. 2 is a close up partial cutaway view of handle 112 of FIG. 1 before retraction of sheath 106. Referring now to FIGS. 1 and 2 together, handle 112 includes a slide ring 124. Rotation of slide ring 124 with respect to longitudinal axis L of handle 112 (axial rotation) as indicated by arrow 126 is converted into axial translation, i.e., retraction, of sheath 106 (as relative rotation of the threaded engagement between pieces causes a linear retraction of the sheath 106). This provides a mechanical advantage between handle 112 and sheath 106, helping the physician to overcome the large static frictional forces between prosthesis 102 and sheath 106. This mechanical advantage also helps overcome any invagination of prosthesis 102 into sheath 106.

FIG. 3 is a close up partial cutaway view of handle 112 of FIG. 2 during retraction of sheath 106. Referring now to FIGS. 2 and 3 together, slide ring 124 includes a distal end 202 and a proximal end 204. Located within and coupled to slide ring 124 is a slide 206. In one embodiment, slide 206 includes a threaded outer surface 208 threadedly attached to a threaded inner surface 210 of slide ring 124.

Initially, slide 206 is located adjacent distal end 202 of slide ring 124 as illustrated in FIG. 2. Axial rotation of slide ring 124 in a direction as indicated by arrow 126 causes axial translation of slide 206 in a proximal direction as indicated by arrow 212 away from distal end 202 and towards proximal end 204 of slide ring 124.

Handle 112 includes a longitudinal axis L. As used herein, axial rotation is rotation around and in a plane perpendicular to longitudinal axis L. Further, axial translation is motion along longitudinal axis L. Axial position is a particular position along longitudinal axis L. Angular position is a particular rotational position around and in a plane perpendicular to longitudinal axis L.

For example, slide 206 is illustrated as being in a first axial position 220 adjacent distal end 202 of slide ring 124 in FIG. 2. Axial rotation of slide ring 124 in a direction as indicated by arrow 126 causes slide 206 to move to a second axial position 222 adjacent proximal end 204 of slide ring 124 as illustrated in FIG. 3.

Sheath 106 is coupled to slide 206 as discussed further below. Accordingly, axial translation of slide 206 is converted into axial translation, i.e., retraction, of sheath 106.

As a result, referring again to FIG. 1, a proximal end 128 of prosthesis 102, which is deployed first, is very gradually released. In this manner, the physician is allowed to verify the accuracy of the deployment position as prosthesis 102 initially engages the surrounding body lumen.

However, since the coefficient of dynamic friction is typically lower than the coefficient of static friction, the frictional resistance force between prosthesis 102 and sheath 106 decreases once sheath 106 begins to move. Additionally, as sheath 106 moves, more and more of prosthesis 102 is exposed by sheath 106, i.e., the area of contact between prosthesis 102 and sheath 106 decreases. For this additional reason, the amount of frictional resistance to movement between prosthesis 102 and sheath 106 decreases once sheath 106 begins to move. Further, once proximal end 128 of prosthesis 102 has firmly engaged the surrounding body lumen, the relationship between prosthesis 102 and the surrounding body lumen is largely set, so that deployment can proceed safely and at a more rapid rate.

Thus, after retraction of sheath 106 is initiated by axial rotation of slide ring 124, retraction of sheath 106 is completed by axially pulling on slide ring 124 to slide ring 124. More particularly, after proximal end 128 of prosthesis 102 is deployed by retracting sheath 106 by rotating slide ring 124, slide ring 124 is easily and quickly slid along longitudinal axis L of handle 112 without further axial rotation of slide ring 124. By sliding slide ring 124, sheath 106 is easily and quickly retracted thus rapidly completing deployment of prosthesis 102. Rapid deployment of prosthesis 102 facilitates faster procedure times, thus minimizing the period of time during which blood flow is occluded.

Sheath 106 is described above as being retracted by the combination of axial rotation of slide ring 124 followed by axial translation, i.e., sliding, of slide ring 124 along longitudinal axis L of handle 112. However, in an alternative embodiment, sheath 106 can be retracted entirely by axial rotation of slide ring 124 (such a mode of retraction is not shown). Further, in yet another alternative embodiment, sheath 106 can be retracted entirely by sliding of slide ring 124 along longitudinal axis L of handle 112 (for example without initiating rotation of the handle in the above described embodiment).

FIG. 4 is a close up partial cutaway view of handle 112 of FIG. 3 during retraction of sheath 106 in accordance with one embodiment of the present invention. Referring now to FIGS. 3 and 4 together, handle 112 includes a slide shaft 402 having a distal end 404 and a proximal end 406. Slide shaft 402 extends between a distal housing 410 and a proximal housing 412 of handle 112. Slide 206 and slide ring 124 are slidably mounted on slide shaft 402.

A diameter D1 of slide shaft 402 is less than a proximal end diameter D2 of distal housing 410 and is less than a diameter D3 of proximal housing 412. Accordingly, slide ring 124 is capable of axial translation along slide shaft 402 between distal housing 410 and proximal housing 412. Stated another way, distal housing 410 forms a forward stop for slide ring 124 and proximal housing 412 forms a rear stop for slide ring 124.

Slide ring 124 is easily and quickly slid along slide shaft 402 of handle 112 from distal housing 410 to proximal housing 412. Since slide 206 is threadedly engaged with (sometimes called threadedly attached) to slide ring 124, axial translation of slide ring 124 produces an axial translation of slide 206. Since slide 206 is coupled to sheath 106, axial translation of slide 206 produces an axial translation of sheath 106. Overall, by sliding slide ring 124, sheath 106 is easily and quickly retracted thus rapidly completing deployment of prosthesis 102.

For example, slide ring 124 is illustrated as being adjacent distal housing 410 of handle 112 in FIG. 3. Axial translation of slide ring 124 as indicated by arrow 320 causes slide ring 124 and slide 206 to move to a third axial position 224 adjacent proximal housing 412 of handle 112 as illustrated in FIG. 4. Sheath 106 is coupled to slide 206. Accordingly, axial translation of slide ring 124 also axially translates, i.e., retracts, sheath 106.

FIG. 5 is a partial cross-sectional view of handle 112 taken at V-V of FIG. 2. FIG. 6 is a cross-sectional view of handle 112 taken at VI-VI of FIG. 5.

In one embodiment, slide ring 124 includes at least two sections joined together. However, in an alternative embodiment, slide ring 124 is integral, i.e., is a single piece not a plurality of pieces connected together.

Referring now to FIGS. 5 and 6 together, slide ring 124 is cylindrical and includes threaded inner surface 210. In one embodiment, threaded inner surface 210 is a cylindrical surface formed with a continuous thread (sometimes called a series of threads), e.g., internal threads.

Slide 206 includes an outer body 502, an inner body 504, and couplers 602, which couple outer body 502 to inner body 504 as discussed further below. In one embodiment, outer body 502 is cylindrical and is outside and encloses slide shaft 402, which is also cylindrical.

Outer body 502 includes threaded outer surface 208. In one embodiment, threaded outer surface 208 is a cylindrical surface formed with a continuous thread (sometimes called a series of threads), e.g., external and helical threads. More particularly, threaded outer surface 208 is a cylindrical surface formed with a continuous series of high points which together form a helical thread pattern.

Threaded outer surface 208 of outer body 502 is threaded with threaded inner surface 210 of slide ring 124. More particularly, the external threads of threaded outer surface 208 are engaged with the internal threads of threaded inner surface 210 of slide ring 124. However, in alternative embodiments, threaded outer surface 208 can be formed with pins, tabs or other protrusions which mate (or engage) with the threads of threaded inner surface 210 of slide ring 124.

Rotation of slide ring 124 with respect to the slide causes slide 206 to move linearly while its threads track along a helical path of the series of threads of threaded inner surface 210 of slide ring 124. More particularly, rotation of slide ring 124 causes threaded outer surface 208 of slide 206 to track the helical path of the series of threads of threaded inner surface 210 of slide ring 124. As threaded outer surface 208 of slide 206 track the helical path of the series of threads of threaded inner surface 210, slide 206 translates in direction 320 (FIG. 4) along longitudinal axis L.

Inner body 504 is inside and located within slide shaft 402. Inner body 504 has a central aperture 506 through which pushrod 104 extends. Pushrod 104 has a guide wire lumen 505 through which a guide wire 116 extends. Proximal end 122 of sheath 106 is attached to inner body 504, for example, using adhesive or screws.

Slide shaft 402 includes opposing slots 604. Couplers 602 extend through slots 604 and couple outer body 502 to inner body 504. By extending through slots 604, couplers 602 prevent rotation of slide 206 and thus of sheath 106 with respect to slide shaft 402.

In one embodiment, slide 206 is integral, i.e., outer body 502, inner body 504, and couplers 602 are parts of a single piece and are not a plurality of separate pieces connected together. However, in an alternative embodiment, outer body 502, inner body 504, and/or couplers 602 are separate pieces connected together. For example, couplers 602 can be set screws, tabs protruding radially inward or outward from outer body 502 and/or inner body 504, respectively.

FIG. 7 is a close up partial cutaway view of handle 112 of FIG. 1 before retraction of sheath 106 in another embodiment according to the present invention. Referring now to FIGS. 1 and 7 together, handle 112 includes a hub assembly 702. Axial rotation of hub assembly 702 in a direction as indicated by arrow 126 is converted into axial translation, i.e., retraction, of sheath 106. This provides a mechanical advantage between handle 112 and sheath 106, helping the physician to overcome the relatively larger static frictional resistance between prosthesis 102 and sheath 106. This mechanical advantage also helps overcome any invagination of prosthesis 102 into sheath 106.

FIG. 8 is a close up partial cutaway view of handle 112 of FIG. 7 during retraction of sheath 106. Referring now to FIGS. 7 and 8 together, hub assembly 702 includes a slide ring 124A and a hub 704. Slide ring 124A, sometimes called a cam-lock ring, is mounted on hub 704. For example, slide ring 124A and hub 704 are molded parts fixedly mounted together.

Hub 704 includes a selectively engaging member 706. By rotating slide ring 124A, selectively engaging member 706 and thus hub assembly 702 is selectively engaged (FIG. 7) and disengaged (FIG. 8) from a pushrod 104A. To illustrate, in one embodiment, selectively engaging member 706 includes an inside threaded surface 708 and pushrod 104A includes a threaded outer surface 710, sometimes called an external threaded surface 710. In one embodiment, inside threaded surface 708 and external threaded surface 710 each include a continuous series of threads, e.g., helical threads. Stated another way, inside threaded surface 708 and external threaded surface 710 each are a continuous thread.

By rotating slide ring 124A in a first direction, e.g., counterclockwise, threaded surface 708 of selectively engaging member 706 is pressed into threaded engagement (attachment) with threaded outer surface 710 of pushrod 104A as illustrated in FIG. 7. Thus, rotation of slide ring 124A in the first direction engages selectively engaging member 706 with pushrod 104A. More generally, rotation of slide ring 124A in the first direction engages and threadably attaches (mounts) hub assembly 702 with pushrod 104A.

Initially, selectively engaging member 706 is engaged with pushrod 104A as illustrated in FIG. 7. Axial rotation of hub assembly 702 in a direction of rotation as indicated by arrow 126 causes axial translation of hub assembly 702 in an axial direction as indicated by arrow 712 away from distal housing 410 and towards proximal housing 412 of handle 112. More particularly, axial rotation of hub assembly 702 causes hub assembly 702 to move along a helical path of the thread of threaded outer surface 710 of pushrod 104A.

For example, hub assembly 702 is illustrated as being in a first axial position 730 adjacent distal housing 410 of handle 112 in FIG. 7. Axial rotation of hub assembly 702 in a direction as indicated by arrow 126 causes hub assembly 702 to move to a second axial position 732 between distal housing 410 and proximal housing 412 of handle 112 as illustrated in FIG. 8. Stated another way, axial rotation of hub assembly 702 causes axial translation of hub assembly 702.

Sheath 106 is coupled to hub assembly 702 as discussed further below. Accordingly, axial translation of hub assembly 702 causes axial translation, i.e., retraction, of sheath 106.

As a result, referring again to FIG. 1, a proximal end 128 of prosthesis 102, which is deployed first, is very gradually released. In this manner, the physician is allowed to verify the accuracy of the deployment position as prosthesis 102 initially engages the surrounding body lumen.

Further, after proximal end 128 of prosthesis 102 is deployed by retracting sheath 106 by rotating hub assembly 702 as discussed above, selectively engaging member 706 is selectively disengaged from pushrod 104A as illustrated in FIG. 8.

In accordance with one embodiment, by rotating slide ring 124A in a second direction opposite the first direction, e.g., clockwise, threaded surface 708 of selectively engaging member 706 is released (retracted) from threaded attachment with threaded outer surface 710 of pushrod 104A. Thus, rotation of slide ring 124A in the second direction disengages selectively engaging member 706, and thus hub assembly 702, from pushrod 104A.

Once disengaged, hub assembly 702 is slidably mounted on pushrod 104A. More particularly, hub assembly 702 is supported around pushrod 104A by sheath 106. Thus, hub assembly 702 is easily and quickly slid along pushrod 104A and longitudinal axis L of handle 112 without further rotation of hub assembly 702. By sliding hub assembly 702, sheath 106 is easily and quickly retracted thus rapidly completing deployment of prosthesis 102. Rapid deployment of prosthesis 102 facilitates faster procedure times, thus minimizing the period of time during which blood flow is occluded.

Sheath 106 is described above as being retracted by the combination of axial rotation of hub assembly 702 followed by sliding, i.e., axial translation, of hub assembly 702 along longitudinal axis L of handle 112. However, in an alternative embodiment, sheath 106 is retracted entirely by axial rotation of hub assembly 702. Further, in yet another embodiment, sheath 106 is retracted entirely by sliding of hub assembly 702 along longitudinal axis L of handle 112.

In yet another embodiment, hub assembly 702 is initially engaged with pushrod 104A. Sheath 106 is initially retracted by axial rotation of hub assembly 702. Hub assembly 702 is then disengaged from pushrod 104A. Sheath 106 is further retracted by sliding of hub assembly 702 along longitudinal axis L of handle 112. Hub assembly 702 is again engaged with pushrod 104A. For example, if the deployment force, e.g., friction, increases and the physician desires more mechanical advantage for further deployment of sheath 106. Sheath 106 is then further retracted by axial rotation of hub assembly 702. In the above manner, sheath 106 is retracted rapidly by sliding of hub assembly 702. However, at any time during retraction, hub assembly 702 can be engaged with pushrod 104A for more mechanical advantage and control of sheath 106.

As shown in FIG. 8, pushrod 104A extends between distal housing 410 and proximal housing 412 of handle 112. In one embodiment, distal housing 410 and proximal housing 412 are connected to and supported by a support member (not shown).

When disengaged, hub assembly 702 is easily and quickly slid along pushrod 104A of handle 112 from distal housing 410 to proximal housing 412. Since hub assembly 702 is coupled to sheath 106, axial translation of hub assembly 702 produces an axial translation of sheath 106. Overall, by sliding hub assembly 702, sheath 106 is easily and quickly retracted thus rapidly completing deployment of prosthesis 102.

For example, hub assembly 702 is illustrated as being at second axial position 732 between distal housing 410 and proximal housing 412 of handle 112 in FIG. 8. Axial translation of hub assembly 702 in a direction as indicated by arrow 720 causes hub assembly 702 to move to a third axial position 734 adjacent proximal housing 412 of handle 112 as indicated by the dashed lines in FIG. 8. Sheath 106 is coupled to hub assembly 702. Accordingly, axial translation of hub assembly 702 causes axial translation, i.e., retraction, of sheath 106.

FIG. 9 is a cross-sectional view of handle 112 taken at IX-IX of FIG. 7. FIG. 10 is a cross-sectional view of handle 112 taken at X-X of FIG. 9.

Referring now to FIGS. 9 and 10 together, hub assembly 702 includes hub 704. Hub 704 includes a cylindrical body 950 and selectively engaging member 706. In accordance with this embodiment, selectively engaging member 706 includes a first spring arm 902A and a second spring arm 902B, collectively spring arms 902. Spring arms 902 terminate at threaded surface 708.

In accordance with this embodiment, spring arms 902A, 902B include upper arms 952A, 952B and lower arms 954A, 954B connected together at elbows 956A, 956B. Upper arms 952A, 952B, lower arms 954A, 954B and elbows 956A, 956B are collectively referred to as upper arms 952, lower arms 954 and elbows 956, respectively.

First ends 958 of upper arms 952 are connected to cylindrical body 950. Second ends 960 of upper arms 952 are connected to first ends 962 of lower arms 954.

Second ends 964 of lower arms 954A, 954B include threaded surfaces 708A, 708B, respectively. Threaded surfaces 708A, 708B are collectively referred to as threaded surface 708.

Sheath 106 is rotationally mounted to hub 704 by a bearing 906. Bearing 906 allows hub assembly 702 including hub 704 to be rotating without imparting any rotation to sheath 106.

Slide ring 124A is rotationally mounted on hub 704. Illustratively, hub 704 includes flanges 908, 910, which fit into tracks 912, 914 of slide ring 124A. Thus, slide ring 124 is mounted on hub 704, yet, is capable of angular rotation relative to hub 704.

Referring now to FIG. 10, slide ring 124A is cylindrical and includes an inner surface 916. Tracks 912, 914 of slide ring 124A are formed in inner surface 916. Slide ring 124A further includes tabs 918A, 918B, collectively tabs 918, protruding inwards from inner surface 916.

Slide ring 124A is in a lock position 1002 in FIG. 10, i.e., is at a particular angular position relative to hub 704. When in lock position 1002, tabs 918 are engaged with and press inwards on spring arms 902. More particularly, elbows 956 of spring arms 902 are seated within notches 926A, 926B, collectively notches 926, of tabs 918A, 918B, respectively, when slide ring 124A is in lock position 1002.

This forces threaded surface 708 of spring arms 902 to engage threaded outer surface 710 of pushrod 104A. In this manner, hub assembly 702 is engaged with pushrod 104A.

To move hub assembly 702 relative to pushrod 104A, hub assembly 702 is rotated. The engagement of threaded surface 708 of selectively engaging member 706 to threaded outer surface 710 of pushrod 104A translates this axial rotation into axial translation of hub assembly 702.

In one embodiment, the direction in which slide ring 124A is rotated to engage hub assembly 702 with pushrod 104A, i.e., the first direction, is the same direction in which hub assembly 702 is rotated to retract sheath 106. In accordance with this embodiment, axial rotation of slide ring 124A in the first direction serves at least two purposes.

First, axial rotation of slide ring 124A seats spring arms 902 within notches 926 to engage threaded surface 708 of selectively engaging member 706 with threaded outer surface 710 of pushrod 104A. Second, once spring arms 902 are seated within notches 926, further axial rotation of slide ring 124A causes rotation of hub 704 and axial translation of hub assembly 702.

FIG. 11 is a cross-sectional view of handle 112 taken at XI-XI of FIG. 8. FIG. 12 is a cross-sectional view of handle 112 taken at XII-XII of FIG. 11.

Referring now to FIGS. 11 and 12 together, slide ring 124A is in an unlock position 1202 in FIG. 12, i.e., is at a second particular angular position relative to hub 704. For example, unlock position 1202 is 90 degrees from lock position 1002. In one embodiment, hub 704 is formed with stops 940A, 940B, collectively stops 940, which protrude outwards from hub 704 and engage tabs 918 to prevent slide ring 124A from being rotated past unlock position 1202.

When in unlock position 1202, tabs 918 are away from and are not engaged with spring arms 902. Spring arms 902 and, more particularly, upper arms 952, are resilient members. In one embodiment, when relaxed, spring arms 902 are positioned away from pushrod 104A. Stated another way, slide ring 124A places spring arms 902 under tension to engage spring arms 902 with pushrod 104A as illustrated in FIG. 10. However, when slide ring 124A is moved to unlock position 1202 as shown in FIG. 12, spring arms 902 return to their relaxed position adjacent inner surface 916 of slide ring 124A.

Thus, when slide ring 124A is in unlock position 1202 as shown in FIG. 12, threaded surface 708 of selectively engaging member 706 is disengaged from threaded outer surface 710 of pushrod 104A. This allows hub assembly 702 to be readily and easily slid along pushrod 104A as discussed above.

FIG. 13 is an enlarged cross-sectional view of the region XIII of FIG. 11 of pushrod 104A of FIG. 11 in accordance with one embodiment of the present invention. In accordance with this embodiment, threads 1302 of threaded outer surface 710 of pushrod 104A are buttress threads. Threads 1302 include angled surfaces 1304 in one direction and flat surfaces 1306 in the other.

Angled surfaces 1304 are at an angle to a plane perpendicular to longitudinal axis L. Stated another way, angled surfaces 1304 are angled relative to the direction normal to longitudinal axis L.

In contrast, flat surfaces 1306 are parallel to a plane perpendicular to longitudinal axis L. Stated another way, flat surfaces 1306 are in the direction normal to longitudinal axis L.

During rotation of hub assembly 702 as discussed above, referring now to FIGS. 9 and 13 together, threaded surface 708 of selectively engaging member 706 is forced against flat surfaces 1306 of pushrod 104A. In this manner, force is applied to selectively engaging member 706 in a direction parallel to longitudinal axis L thus causing axial translation of hub assembly 702. However, there is essentially no force applied to selectively engaging member 706 in the direction normal to longitudinal axis L. This essentially eliminates the possibility of spring arms 902 being forced apart and the associated slipping of hub assembly 702 on pushrod 104A.

However, in an alternative embodiment, threads 1302 are formed, for example, in a conventional profile, to impart force to selectively engaging member 706 in the direction normal to longitudinal axis L. For example, when a high load is imparted to hub assembly 702, e.g., when sheath 106 is stuck, spring arms 902 are forced apart and hub assembly 702 slips on pushrod 104A. This prevents damage to sheath 106 and complications in the deployment of prosthesis 112 (FIG. 1).

As discussed above, selectively engaging member 706 includes two spring arms 902, i.e., spring arms 902A, 902B, as shown in FIGS. 9 and 10. Spring arms 902 extend around and contact approximately two-thirds of the circumference of pushrod 104A. However, in one embodiment, selectively engaging member 706 includes only spring arm 902A or spring arm 902B, and not both. In yet another embodiment, selectively engaging member 706 includes three or more spring arms 902.

In yet other alternative embodiments, selectively engaging member 706 is a spring-loaded mechanism. This spring-loaded mechanism is biased such that it is engaged or disengaged with pushrod 104A when the spring-loaded mechanism is in its relaxed state. For example, the spring-loaded mechanism includes a screw that is engaged with pushrod 104A when the spring-loaded mechanism is in its relaxed position. The spring-loaded mechanism further includes a button, which is pressed to disengaged the screw. This button is integrated into hub assembly 702, or is mounted as a separate button or a trigger-type mechanism. However, other spring-loaded mechanisms are used in other embodiments.

Further, in one embodiment, a ratchet or pawl is used to prevent unintentional or undesirable axial rotation or axial translation. For example, a ratchet or pawl is used to prevent slide rings 124, 124A (FIGS. 2, 7) from axial rotation in the direction opposite arrow 126. As a further example, a ratchet or pawl is used to prevent slide ring 124, hub assembly 702 (FIGS. 4, 8) from moving backwards toward distal housing 410.

FIGS. 14 and 15 are perspective and side views of another embodiment of delivery system 100B according to the present invention. FIG. 16 is a side view, partially in cross-section, of delivery system 100B of FIGS. 14 and 15 after retraction of a sheath 106B.

Referring now to FIGS. 14, 15 and 16 together, delivery system 100B includes a handle 112B. Handle 112B includes a distal housing 1402, sometimes called a front grip, a hub assembly 1404, sometimes called an external slider, and a proximal housing 1406, sometimes called a rear grip. Handle 112B further includes a slide shaft 1408, sometimes called a screw gear, extending between distal housing 1402 and proximal housing 1406.

Slide shaft 1408 is a hollow tubular member and includes opposing slots 1410 (FIG. 14). Slide shaft 1408 includes a threaded outer surface 1412, e.g., a buttress thread.

Hub assembly 1404 is selectively engaged and disengaged with threaded outer surface 1412 of slide shaft 1408 by motion of a thumb slider 1414, sometimes called an actuation button.

When engaged, i.e., threadedly attached, with threaded outer surface 1412 of slide shaft 1408, axial rotation of hub assembly 1404 as indicated by arrow 126 (FIG. 14) is converted into axial translation, i.e., retraction, of sheath 106B of delivery system 100B. Sheath 106B is coupled to hub assembly 1404.

As a result, a proximal end 128B (FIG. 16) of a prosthesis 102B, which is deployed first, is very gradually released through axial rotation of hub assembly 1404. In this manner, the physician is allowed to verify the accuracy of the deployment position as prosthesis 102B initially engages the surrounding body lumen.

Further, when disengaged from threaded outer surface 1412 of slide shaft 1408, hub assembly 1404 is slidably mounted on slide shaft 1408. When hub assembly 1404 is slidably mounted on slide shaft 1408, hub assembly 1404 is easily and quickly slid along slide shaft 1408. By sliding hub assembly 1404, sheath 106B is easily and quickly retracted thus rapidly completing deployment of prosthesis 102B. Rapid deployment of prosthesis 102B facilitates faster procedure times, thus minimizing the period of time during which blood flow is occluded.

Sheath 106B is described above as being retracted by the combination of axial rotation of hub assembly 1404 followed by sliding, i.e., axial translation, of hub assembly 1404 along a longitudinal axis L of handle 112B. However, in an alternative embodiment, sheath 106B is retracted entirely by axial rotation of hub assembly 1404. Further, in yet another embodiment, sheath 106B is retracted entirely by sliding of hub assembly 1404 along longitudinal axis L of handle 112B.

In yet another embodiment, hub assembly 1404 is initially engaged with threaded outer surface 1412 of slide shaft 1408. Sheath 106B is initially retracted by axial rotation of hub assembly 1404.

Hub assembly 1404 is then disengaged from threaded outer surface 1412 of slide shaft 1408. Sheath 106B is further retracted by sliding of hub assembly 1404 along longitudinal axis L of handle 112B.

Hub assembly 1404 is again engaged with threaded outer surface 1412 of slide shaft 1408, for example, if the deployment force, e.g., friction, increases and the physician desires more mechanical advantage for further deployment of sheath 106B. Sheath 106B is then further retracted by axial rotation of hub assembly 1404. In the above manner, sheath 106B is retracted rapidly by sliding of hub assembly 1404. However, at any time during retraction, hub assembly 1404 can be engaged with threaded outer surface 1412 of slide shaft 1408 for more mechanical advantage and control of sheath 106B.

FIG. 17 is an enlarged side view, partially in cross-section, of the region XVII of handle 112B of FIG. 16. Referring now to FIG. 17, sheath 106B extends through a strain relief 1702 at a distal end 1704 of distal housing 1402. Strain relief 1702 distributes stress from distal housing 1402 onto sheath 106B thus preventing kinking or other damage to sheath 106B at the location where the sheath tube exits the front grip. Sheath 106B is coupled to a slide 1706 of hub assembly 1404.

Slide (T-tube assembly) 1706 is in the shape of a T and includes an outer body (two oppositely positioned members) 1708, an inner body (tube) 1710, and couplers (two oppositely extending members(fins)) 1712, which couple outer body 1708 to inner body 1710 as discussed further below. In one embodiment, outer body 1708 is outside of a cylindrical slide shaft 1408.

Outer body 1708 is slidably mounted within a circumferential channel 1714 of an external housing 1716 of hub assembly 1404. More particularly, circumferential channel 1714 is defined by a distal annular stop 1718, a proximal annular stop 1720, and a tapering cylindrical portion 1722 of external housing 1716.

Distal and proximal annular stops 1718 and 1720 prevent longitudinal motion of outer body 1708 and thus slide 1706 relative to external housing 1716. However, external housing 1716 is rotatable relative to outer body 1708 and thus slide 1706. More particularly, as external housing 1716 is rotated, outer body 1708 though rotationally stationary slides within rotating circumferential channel 1714.

Inner body (tube) 1710 is inside and located within slide shaft 1408. Inner body 1710 includes central aperture 1724 through which a pushrod 104B extends. The proximal end of sheath 106B is attached to inner body (tube) 1710, for example, using adhesive or screws. The distal end of the inner body include one or more support rings; e.g., 1710A, 1710B; which prevent the collapse or deflection of the side walls of the slotted portion of the slide shaft 1408 when engaged by the hub assembly.

As set forth above, slide shaft 1408 includes opposing slots 1410. Couplers 1712 extend through slots 1410 and couple outer body 1708 to inner body 1710. By extending through slots 1410, couplers 1712 prevent rotation of slide 1706 and thus of sheath 106B with respect to slide shaft 1408.

In one embodiment, slide 1706 is integral, i.e., outer body 1708, inner body 1710, and couplers 1712 are parts of a single piece and are not a plurality of separate pieces connected together. However, in an alternative embodiment, outer body 1708, inner body 1710, and/or couplers 1712 are separate pieces connected together.

Hub assembly 1404 further includes an internal slider subassembly 1730, sometimes called a selectively engaging member. With the exception of thumb slider 1414, the internal slider subassembly 1730 is located within external housing 1716. Thumb slider 1414 is part of a sleeve 1732 of internal slider subassembly 1730 and extends through a thumb slider slot 1734 of external housing 1716. Thumb slider 1414, and thus sleeve 1732 of internal slider subassembly 1730 are moved, e.g., by the physician, relative to external housing 1716 to selectively engage and disengage hub assembly 1404 from threaded outer surface 1412 of slide shaft 1408.

FIGS. 18, 19 and 20 are side, top and exploded views of internal slider subassembly 1730. Referring now to FIGS. 18, 19 and 20, internal slider subassembly 1730 includes an inner slider 1802, a pair of opposing thread teeth 1804A, 1804B, a spring 1806, and a spring retainer 1808. Although two thread teeth 1804A, 1804B are illustrated and discussed below, other numbers of thread teeth 1804 and corresponding structure are used in other embodiments, e.g., one, three, four, five or more.

Referring now to FIG. 20, inner slider 1802 includes a generally cylindrical body 1810, a distal stop 1812, and a proximal spring retainer mounting section 1814.

Body 1810 includes a pair of opposing distal thread teeth pivot apertures 1816A, 1816B, a pair of opposing proximal thread teeth pivot apertures 1818A, 1818B, and a pair of opposing thread teeth flat (not arc shaped) pivot supports 1820A, 1820B (proximal thread tooth pivot aperture 1818B and thread tooth pivot support 1820B are not illustrated in the view of FIG. 20, see FIGS. 21 and 22). Collectively, distal thread teeth pivot apertures 1816A, 1816B, proximal thread teeth pivot apertures 1818A, 1818B, and thread teeth pivot supports 1820A, 1820B are sometimes referred to as distal or first thread teeth pivot apertures 1816, proximal or second thread teeth pivot apertures 1818, and thread teeth pivot supports 1820, respectively.

Thread tooth pivot support 1820A approximates a circumferential member, i.e., has a length along the circumference of body 1810, but actually is a flat element (like the chord of a circle to the linear pivot axis). However, in another embodiment, tooth pivot support 1820A is a curved circumferential member, e.g., a segment of a circle. Thread tooth pivot support 1820A is between and separates distal thread tooth pivot aperture 1816A and proximal thread tooth pivot aperture 1818A.

Thread tooth pivot support 1820A includes a protruding pivot pin 1822A, which seats in a pivot pin aperture 1824A of thread tooth 1804A although in one embodiment, pivot pin 1822A and pivot pin aperture 1824A are not used. Accordingly, thread tooth 1804A is pivotally mounted to thread tooth pivot support 1820A and thus inner slider 1802.

As discussed further below, thread tooth 1804A pivots back and forth (proximally and distally) on thread tooth pivot support 1820A into and out of proximal thread tooth pivot aperture 1818A and distal thread tooth pivot aperture 1816A.

Thread tooth pivot support 1820B (see FIG. 21) is similar to thread tooth pivot support 1820A. Thread tooth pivot support 1820B is between and separates distal thread tooth pivot aperture 1816B and proximal thread tooth pivot aperture 1818B.

Thread tooth pivot support 1820B includes a protruding pivot pin 1822B (see FIG. 21), which seats in a pivot pin aperture 1824B of thread tooth 1804B although in one embodiment, pivot pin 1822B and pivot pin aperture 1824B are not used. Accordingly, thread tooth 1804B is pivotally mounted to thread tooth pivot support 1820B and thus inner slider 1802.

As discussed further below, thread tooth 1804B pivots back and forth (proximally and distally) on thread tooth pivot support 1820B into and out of proximal thread tooth pivot aperture 1818B and distal thread tooth pivot aperture 1816B.

Sleeve 1732 includes a pair of opposing proximal thread teeth pivot apertures 1830A, 1830B, a pair of opposing distal thread teeth pivot cutouts 1832A, 1832B, and a pair of opposing thread teeth press members 1834A, 1834B. Collectively, proximal thread teeth pivot apertures 1830A, 1830B, distal thread teeth pivot cutouts 1832A, 1832B, and thread teeth press members 1834A, 1834B are sometimes referred to as proximal thread teeth pivot apertures 1830, distal thread teeth pivot cutouts 1832, and thread teeth press members 1834, respectively.

Sleeve 1732 is generally cylindrical and has an inner diameter slightly greater than an outer diameter of body 1810 of inner slider 1802. This allows sleeve 1732 to be slipped over and located around body 1810 of inner slider 1802.

One or more longitudinal lips 1836 protrude inwards from an inner surface 1838 of sleeve 1732. Lips 1836 mate with longitudinal slots 1840 in an outer surface 1842 of body 1810 of inner slider 1802. Slots 1840 have a greater length than lips 1836 allowing lips 1836 to be slid longitudinally back and forth within slots 1840. In this manner, longitudinal motion of sleeve 1732 relative to inner slider 1802 is permitted while rotation of sleeve 1732 relative to inner slider 1802 is prevented.

Thread tooth press member 1834A is a circumferential member, i.e., has a length along the circumference of sleeve 1732. Thread tooth press member 1834A is between and separates distal thread tooth pivot cutout 1832A and proximal thread tooth pivot aperture 1830A.

As discussed further below, thread tooth press member 1834A presses on and pivots thread tooth 1804A back and forth as sleeve 1732 is moved longitudinally relative to inner slider 1802.

Similarly, thread tooth press member 1834B is a circumferential member, i.e., has a length along the circumference of sleeve 1732. Thread tooth press member 1834B is between and separates distal thread tooth pivot cutout 1832B and proximal thread tooth pivot aperture 1830B.

As discussed further below, thread tooth press member 1834B presses on and pivots thread tooth 1804B back and forth as sleeve 1732 is moved longitudinally relative to inner slider 1802.

Spring retainer 1808 is mounted around spring retainer mounting section 1814 of inner slider 1802. Spring 1806 is mounted around inner slider 1802 and is located longitudinally between sleeve 1732 and a proximal spring stop 1844 of spring retainer 1808.

Spring 1806 is compressed between spring stop 1844 of spring retainer 1808 and a proximal end 1846 of sleeve 1732. Due to this compression of spring 1806, spring 1806 urges sleeve 1732 distally and against distal stop 1812 of inner slider 1802.

Distal stop 1812 of inner slider 1802 includes opposing cutouts 1848A, 1848B, collectively cutouts 1848. Thread teeth 1804A, 1804B include extending fingers 1850A, 1850B, collectively fingers 1850, which seat in cutouts 1848A, 1848B, respectively as thread teeth 1804 are pivoted. Further, thread teeth 1804A, 1804B include inward protruding teeth 1852A, 1852B, collectively protruding teeth 1852, respectively.

FIG. 21 is a cross-sectional and partially cutaway view of handle 112B along the line XXI-XXI of FIG. 18 with hub assembly 1404 engaged with threaded outer surface 1412 of slide shaft 1408. Referring now to FIG. 21, thread teeth press members 1834 are pressing on thread teeth 1804 opposite of protruding teeth 1852. More particularly, thread teeth press members 1834 press protruding teeth 1852 into threaded engagement with threaded outer surface 1412, e.g., a helical thread pattern, of slide shaft 1408. As shown in FIG. 21, thread teeth 1804 are pivoted distally and into distal thread teeth pivot apertures 1816 of inner slider 1802.

In FIG. 21, the inner body (tube) 1710 with its supports 1710A, 1710B are shown connected to the sheath 106B which is shown partially cutaway. Sheath 106B is a hollow tube and includes a pushrod lumen. Pushrod 104B extends through sheath 106B. Pushrod 104B is also shown partially cutaway. Pushrod 104B is a hollow tube and includes a lumen. A guidewire lumen 2102 extends through pushrod 104B. Guidewire lumen 2102 is a hollow tube and includes a lumen. Guidewire lumen 2102 is also shown partially cutaway. A guidewire 2104 extends through guidewire lumen 2102. In FIG. 22, pushrod 104B, guidewire lumen 2102 and guidewire 2104 are not illustrated for clarity of presentation.

FIG. 22 is a cross-sectional view of handle 112B of FIG. 21 with hub assembly 1404 disengaged from threaded outer surface 1412 of slide shaft 1408. Referring now to FIGS. 21 and 22 together, thread teeth 1804 are curved members. Accordingly, when thread teeth 1804 are located in distal thread teeth pivot apertures 1816 (FIG. 21), thread teeth 1804 pivot on thread teeth pivot supports 1820 and protrude above proximal thread teeth pivot apertures 1818 of inner slider 1802 and into proximal thread teeth pivot apertures 1830 of sleeve 1732. Conversely, when thread teeth 1804 are located in proximal thread teeth pivot apertures 1818 (FIG. 22), thread teeth 1804 pivot on thread teeth pivot supports 1820 and protrude above distal thread teeth pivot apertures 1816 of inner slider 1802 and into distal thread teeth cutouts 1832 of sleeve 1732.

Thread teeth 1804 are pivoted on thread teeth pivot supports 1820 as sleeve 1732 is slid longitudinally, e.g., by pulling or releasing thumb slider 1414 (see FIG. 17). Specifically, when sleeve 1732 is slid proximally by the physician pulling on thumb slider 1414, thread teeth press members 1834 slide proximally on thread teeth 1804. As thread teeth press members 1834 slide proximally on thread teeth 1804 longitudinally past thread teeth pivot supports 1820, thread teeth press members 1834 pivot thread teeth 1804 and move protruding teeth 1852 out of threaded engagement with threaded outer surface 1412 of slide shaft 1408 such that protruding teeth 1852 are spaced apart from threaded outer surface 1412 as shown in FIG. 22.

Conversely, when sleeve 1732 is slid distally, e.g., by spring 1806 upon the physician releasing thumb slider 1414, thread teeth press members 1834 slide distally on thread teeth 1804. As thread teeth press members 1834 slide distally on thread teeth 1804 longitudinally past thread teeth pivot supports 1820, thread teeth press members 1834 pivot thread teeth 1804 and move protruding teeth 1852 into threaded engagement with threaded outer surface 1412 of slide shaft 1408 as shown in FIG. 21.

FIGS. 23 and 24 are exploded and side views, respectively, of a graft cover subassembly and RO radiopaque marker 2300 of delivery system 100B. Illustrative descriptions of the various elements shown in FIGS. 23 and 24 are set forth below in table 1.

TABLE 1

| ELEMENT | DESCRIPTION |
| --- | --- |
| 23-4 | O-ring |
| 23-6 | Graft cover |
| 23-7 | T-tube subassembly |
| 23-8 | Hub cap |
| 23-11 | RO marker |

FIGS. 25 and 26 are exploded and side views, respectively, of a strain relief subassembly 2500 of delivery system 100B. Strain relief subassembly 2500 protects Illustrative descriptions of the various elements shown in FIGS. 25 and 26 are set forth below in table 2.

TABLE 2

| ELEMENT | DESCRIPTION |
| --- | --- |
| 34-9 | Strain relief tubing |
| 34-10 | Strain relief |

This disclosure provides exemplary embodiments of the present invention. The scope of the present invention is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A method comprising:
engaging a hub assembly of a handle to a threaded outer surface of a slide shaft of said handle, wherein said slide shaft extends between a distal housing of said handle and a proximal housing of said handle;
rotating said hub assembly to cause axial translation of said hub assembly and a sheath coupled to said hub assembly relative to a pushrod and prosthesis inside of said sheath, wherein said slide shaft comprises slots, said sheath being coupled to a slide of said hub assembly, said slide extending through said slots;
disengaging said hub assembly from said threaded outer surface by pivoting a thread tooth of said hub assembly out of threaded engagement with said threaded outer surface; and
sliding said hub assembly on said slide shaft to further retract said sheath.

2. A method comprising:
engaging a hub assembly of a handle to a threaded outer surface of a slide shaft of said handle;
rotating said hub assembly to cause axial translation of said hub assembly and a sheath coupled to said hub assembly relative to a pushrod and prosthesis inside of said sheath;
disengaging said hub assembly from said threaded outer surface by pivoting a thread tooth of said hub assembly out of threaded engagement with said threaded outer surface, wherein said hub assembly further comprises a sleeve and an inner slider, said disengaging comprising moving said sleeve relative to said inner slider; and
sliding said hub assembly on said slide shaft to further retract said sheath.

3. The method of claim 2 wherein said disengaging comprises pulling a thumb slider of said hub assembly.

4. The method of claim 3 wherein said pulling comprises sliding a thread tooth press member across said thread tooth.

5. The method of claim 4 wherein said thread tooth press member pivots said thread tooth as said thread tooth press member is slid past a thread tooth pivot support pivotally coupled to said thread tooth.

6. The method of claim 2 wherein said prosthesis is located over said pushrod and restrained within said sheath.

7. The method of claim 6 wherein said rotating comprising retracting said sheath to initiate deployment of said prosthesis.

8. The method of claim 7 wherein said sliding comprising completing said deployment of said prosthesis.

9. The method of claim 2 wherein said pushrod comprises a guide wire lumen.

10. The method of claim 9 wherein a guidewire extends through said guide wire lumen.

11. The method of claim 2 wherein said slide shaft extends between a distal housing of said handle and a proximal housing of said handle.

12. The method of claim 2 wherein said thread tooth is pivotally mounted to a thread tooth pivot support facilitating proximal and distal pivoting of said thread tooth.

13. The method of claim 2 wherein said sleeve comprises a thread tooth press member pressing on said thread tooth.

14. The method of claim 13 wherein said thread tooth press member presses on said thread tooth opposite a protruding tooth of said thread tooth when said hub assembly is engaged to said threaded outer surface.

15. The method of claim 13 wherein said thread tooth is pivoted distally into threaded engagement with said threaded outer surface by said thread tooth press member.

16. The method of claim 13 wherein said disengaging comprises sliding said thread tooth press member past a thread tooth pivot support of said inner slider, said thread tooth being pivotally mounted to said thread tooth pivot support.

17. The method of claim 16 wherein said thread tooth press member proximally pivots said thread tooth as said thread tooth press member is slid past said thread tooth pivot support.

18. The method of claim 17 wherein said thread tooth is proximally pivoted out of threaded engagement with said threaded outer surface.

19. The method of claim 17 wherein said thread tooth is proximally pivoted such that a protruding tooth of said thread tooth is spaced apart from said threaded outer surface.

* * * * *

UNITED STATES PATENT AND TRADEMARK OFFICE
CERTIFICATE OF CORRECTION

PATENT NO.        : 7,419,501 B2
APPLICATION NO.   : 11/460551
DATED             : September 2, 2008
INVENTOR(S)       : Brian Shiu et al.

It is certified that error appears in the above-identified patent and that said Letters Patent is hereby corrected as shown below:

On the title page, item (12) and (75), "Chiu et al." should be changed to -- Shiu et al. --

Signed and Sealed this

Tenth Day of November, 2009

David J. Kappos
*Director of the United States Patent and Trademark Office*